United States Patent
Chichak et al.

(10) Patent No.: US 11,560,526 B2
(45) Date of Patent: *Jan. 24, 2023

(54) THERMALLY STABLE MACROMOLECULAR COMPOUND AND PETROLEUM COMPOSITION INCLUDING THE SAME

(71) Applicant: SI Group, Inc., Schenectady, NY (US)

(72) Inventors: Kelly S. Chichak, Halfmoon, NY (US); Joseph T. Doane, Rotterdam Junction, NY (US); Brian Christofel, Glenville, NY (US); Elliott W. Shanklin, Altamont, NY (US)

(73) Assignee: SI Group, Inc., The Woodlands, TX (US)

( * ) Notice: Subject to any disclaimer, the term of this patent is extended or adjusted under 35 U.S.C. 154(b) by 406 days.

This patent is subject to a terminal disclaimer.

(21) Appl. No.: 16/293,878

(22) Filed: Mar. 6, 2019

(65) Prior Publication Data

US 2019/0276759 A1    Sep. 12, 2019

Related U.S. Application Data

(60) Provisional application No. 62/799,858, filed on Feb. 1, 2019, provisional application No. 62/795,262, filed
(Continued)

(51) Int. Cl.
*C10L 1/198* (2006.01)
*C10L 10/16* (2006.01)
(Continued)

(52) U.S. Cl.
CPC ............ *C10L 1/1981* (2013.01); *C07C 39/06* (2013.01); *C07C 39/15* (2013.01); *C08G 8/08* (2013.01);
(Continued)

(58) Field of Classification Search
CPC .................................................... C10L 1/1981
See application file for complete search history.

(56) References Cited

U.S. PATENT DOCUMENTS

| 4,151,069 A | 4/1979 | Rossi |
| 4,514,314 A | 4/1985 | Rossi |

(Continued)

FOREIGN PATENT DOCUMENTS

| WO | WO2005054321 | 6/2005 |
| WO | WO2017120286 | 7/2017 |

(Continued)

OTHER PUBLICATIONS

Ghaffar et al., "Synthesis of Poly(dodecyl phenol formaldehyde)-b-poly(oxypropylene) Block Copolymer, and Evaluation as Asphaltene Inhibitor and Dispersant," Springer Link, Jan. 2015, vol. 41, Issue 1, pp. 443-455.

(Continued)

Primary Examiner — Ellen M Mcavoy
Assistant Examiner — Ming Cheung Po
(74) Attorney, Agent, or Firm — Dority & Manning, P.A.

(57) ABSTRACT

In one embodiment, an alkylphenol copolymer is disclosed wherein the copolymer comprises at least one alkylphenol monomer and the alkylphenol copolymer exhibits the following: an oscillation displacement Θ of greater than 0 at a temperature of −5° C. in a first oscillation temperature sweep and an oscillation displacement Θ in a second oscillation temperature sweep within 25% of the oscillation displacement Θ in the first oscillation temperature sweep at a temperature of −5° C. In a further embodiment, a petroleum composition is disclosed wherein the composition comprises a petroleum source and a macromolecular compound wherein the macromolecular compound exhibits the following: an oscillation displacement Θ of greater than 0 at a (Continued)

temperature of −10° C. in a first oscillation temperature sweep, and an oscillation displacement Θ in a second oscillation temperature sweep within 25% of the oscillation displacement Θ in the first oscillation temperature sweep at a temperature of −10° C.

17 Claims, 9 Drawing Sheets

Related U.S. Application Data on Jan. 22, 2019, provisional application No. 62/671,728, filed on May 15, 2018, provisional application No. 62/671,800, filed on May 15, 2018, provisional application No. 62/671,850, filed on May 15, 2018, provisional application No. 62/639,037, filed on Mar. 6, 2018.

(51) Int. Cl.
  *C10L 1/195* (2006.01)
  *C08G 8/10* (2006.01)
  *C08G 8/08* (2006.01)
  *C08L 61/06* (2006.01)
  *C10G 75/02* (2006.01)
  *C10G 71/00* (2006.01)
  *C10G 75/04* (2006.01)
  *C07C 39/06* (2006.01)
  *C07C 39/15* (2006.01)

(52) U.S. Cl.
  CPC .............. *C08G 8/10* (2013.01); *C08L 61/06* (2013.01); *C10G 71/00* (2013.01); *C10G 75/02* (2013.01); *C10G 75/04* (2013.01); *C10L 1/195* (2013.01); *C10L 10/16* (2013.01); *C10G 2300/206* (2013.01); *C10G 2300/80* (2013.01)

(56) References Cited

U.S. PATENT DOCUMENTS

| | | | |
|---|---|---|---|
| 5,021,498 A | 6/1991 | Stephenson et al. | |
| 5,039,437 A | 8/1991 | Martella et al. | |
| 5,494,607 A | 2/1996 | Manek et al. | |
| 5,571,506 A | 11/1996 | Regan et al. | |
| 5,851,429 A | 12/1998 | Magyar | |
| 6,180,683 B1 | 1/2001 | Miller et al. | |
| 7,417,009 B2 | 8/2008 | Shmakova-Lindeman | |
| 10,961,474 B2* | 3/2021 | Chichak | C08L 61/06 |
| 10,961,475 B2* | 3/2021 | Doane | C07C 39/15 |
| 10,961,476 B2* | 3/2021 | Chichak | C08L 61/06 |
| 2003/0171221 A1 | 9/2003 | Feustel et al. | |
| 2004/0058827 A1 | 3/2004 | Jennings | |
| 2004/0266973 A1 | 12/2004 | Strickland et al. | |
| 2008/0306314 A1 | 12/2008 | Moreton et al. | |
| 2013/0150272 A1 | 6/2013 | Sonne et al. | |
| 2014/0336285 A1 | 11/2014 | Cendejas Santana et al. | |
| 2017/0292657 A1* | 10/2017 | Kundu | F17D 3/12 |
| 2017/0355798 A1 | 12/2017 | Kundu et al. | |
| 2019/0177630 A1* | 6/2019 | Nguyen | C10L 1/143 |
| 2019/0276660 A1* | 9/2019 | Doane | C08G 8/12 |
| 2019/0276755 A1* | 9/2019 | Chichak | C10G 75/02 |
| 2019/0276756 A1* | 9/2019 | Chichak | C08G 8/08 |

FOREIGN PATENT DOCUMENTS

| | | |
|---|---|---|
| WO | WO2017177009 | 10/2017 |
| WO | WO2018190917 | 10/2018 |
| WO | WO2019005680 | 1/2019 |

OTHER PUBLICATIONS

Venkatesan et al., "The Strength of Paraffin Gels Formed Under Static and Flow Conditions," Chemical Engineering Science 60 (2005) 3587-3598.
International Search Report and Written Opinion for PCT/US2019/020937, dated Jun. 18, 2019, 7 pages.
Goual et al., "Asphaltene aggregation and impact of alkylphenols," Langmuir, 2014, vol. 30, No. 19, pp. 5394-5403.
Related Applications Form.
European Search Report for EP19764607.8 dated Dec. 7, 2021, 11 pages.

* cited by examiner

THERMALLY STABLE MACROMOLECULAR COMPOUND AND PETROLEUM COMPOSITION INCLUDING THE SAME

RELATED APPLICATIONS

This application claims filing benefit of U.S. Provisional Patent Application No. 62/639,037 having a filing date of Mar. 6, 2018, U.S. Provisional Patent Application No. 62/671,728 having a filing date of May 15, 2018, U.S. Provisional Patent Application No. 62/671,800 having a filing date of May 15, 2018, U.S. Provisional Patent Application No. 62/671,850 having a filing date of May 15, 2018, U.S. Provisional Patent Application No. 62/795,262 having a filing date of Jan. 22, 2019, and U.S. Provisional Patent Application No. 62/799,858 having a filing date of Feb. 1, 2019, all of which are hereby incorporated by reference in their entirety.

BACKGROUND OF THE INVENTION

Various additives are traditionally employed during oil production to modify the flow properties of a petroleum source or to inhibit the deposition of certain undesirable byproducts onto surfaces. For example, paraffin inhibitors, asphaltene dispersants, and scale inhibitors may be selectively injected into wells or flowlines to treat a petroleum source and prevent or control the effects of precipitation of paraffins, asphaltenes, and mineral scale. These additives can also be used at other points of the oil production cycle, such as during transportation or storage to limit the deposition of solids on the surface of pipes, storage vessels, and transportation vessels (rail cars, ocean tankers, etc.). Unfortunately, because most conventional additives have limited functionality, operators typically need to add multiple different additives to a petroleum source during a production cycle. For example, one additive might be required to disperse or inhibit the crystallization or surface deposition of paraffin waxes, while a completely separate additive might be required to help disperse or inhibit the precipitation of asphaltenes within the petroleum source or deposition of asphaltenes on contacted surfaces. In addition, such additives may experience various shifts in temperature between production and end-use thereby affecting their use for paraffin inhibition, asphaltene dispersion, etc. As such, a need continues to exist for an additive that is capable of exhibiting a broad spectrum of benefits, particularly when added to a petroleum source, and is thermally stable.

SUMMARY OF THE INVENTION

In accordance with one embodiment of the present invention, an alkylphenol copolymer is disclosed. The alkylphenol copolymer comprises at least one alkylphenol monomer, wherein the alkylphenol copolymer exhibits the following: an oscillation displacement $\Theta$ of greater than 0 at a temperature of $-5°$ C. in a first oscillation temperature sweep and an oscillation displacement $\Theta$ in a second oscillation temperature sweep within 25% of the oscillation displacement in the first oscillation temperature sweep at a temperature of $-5°$ C., wherein the first oscillation temperature sweep starts at 30° C. and ends at either $-20°$ C. or an oscillation displacement $\Theta$ of 0 and is conducted with a stress of 0.4 Pa at an angular frequency of 0.25 rad/s and each subsequent oscillation temperature sweep starts at 25° C. and ends at either $-20°$ C. or an oscillation displacement $\Theta$ of 0 and is conducted with a stress of 0.4 Pa at an angular frequency of 0.25 rad/s.

In accordance with another embodiment of the present invention, a petroleum composition is disclosed. The petroleum composition comprises a petroleum source and a macromolecular compound wherein the macromolecular compound exhibits the following: an oscillation displacement $\Theta$ of greater than 0 at a temperature of $-10°$ C. in a first oscillation temperature sweep, and an oscillation displacement $\Theta$ in a second oscillation temperature sweep within 25% of the oscillation displacement $\Theta$ in the first oscillation temperature sweep at a temperature of $-10°$ C., wherein the first oscillation temperature sweep starts at 30° C. and ends at either $-20°$ C. or an oscillation displacement $\Theta$ of 0 and is conducted with a stress of 0.4 Pa at an angular frequency of 0.25 rad/s and each subsequent oscillation temperature sweep starts at 25° C. and ends at either $-20°$ C. or an oscillation displacement $\Theta$ of 0 and is conducted with a stress of 0.4 Pa at an angular frequency of 0.25 rad/s.

Other features and aspects of the present invention are set forth in greater detail below.

Definitions

It is to be understood that the terminology used herein is for the purpose of describing particular embodiments only and is not intended to limit the scope of the present invention.

"Alkyl" refers to monovalent saturated aliphatic hydrocarbyl groups and "$C_{x-y}$alkyl" refers to alkyl groups having from x to y carbon atoms. This term includes, by way of example, linear and branched hydrocarbyl groups, such as butyl ($CH_3(CH_2)_3$), octyl ($CH_3(CH_2)_7$), nonyl ($CH_3(CH_2)_8$), decyl ($CH_3(CH_2)_9$), undecyl ($CH_3(CH_2)_{10}$), dodecyl ($CH_3(CH_2)_{11}$), tridecyl ($CH_3(CH_2)_{12}$), tetradecyl ($CH_3(CH_2)_{13}$), pentadecyl ($CH_3(CH_2)_{14}$), hexadecyl ($CH_3(CH_2)_{15}$), heptadecyl ($CH_3(CH_2)_{16}$), octadecyl ($CH_3(CH_2)_{17}$), nonadecyl ($CH_3(CH_2)_{18}$), icosanyl ($CH_3(CH_2)_{19}$), henicosanyl ($CH_3(CH_2)_{20}$), docosanyl ($CH_3(CH_2)_{21}$), tricosanyl ($CH_3(CH_2)_{22}$), tetracosanyl ($CH_3(CH_2)_{23}$), pentacosanyl ($CH_3(CH_2)_{24}$), hexacosanyl ($CH_3(CH_2)_{25}$), heptacosanyl ($CH_3(CH_2)_{26}$), octacosanyl ($CH_3(CH_2)_{27}$), etc.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

DETAILED DESCRIPTION

Figure 1:
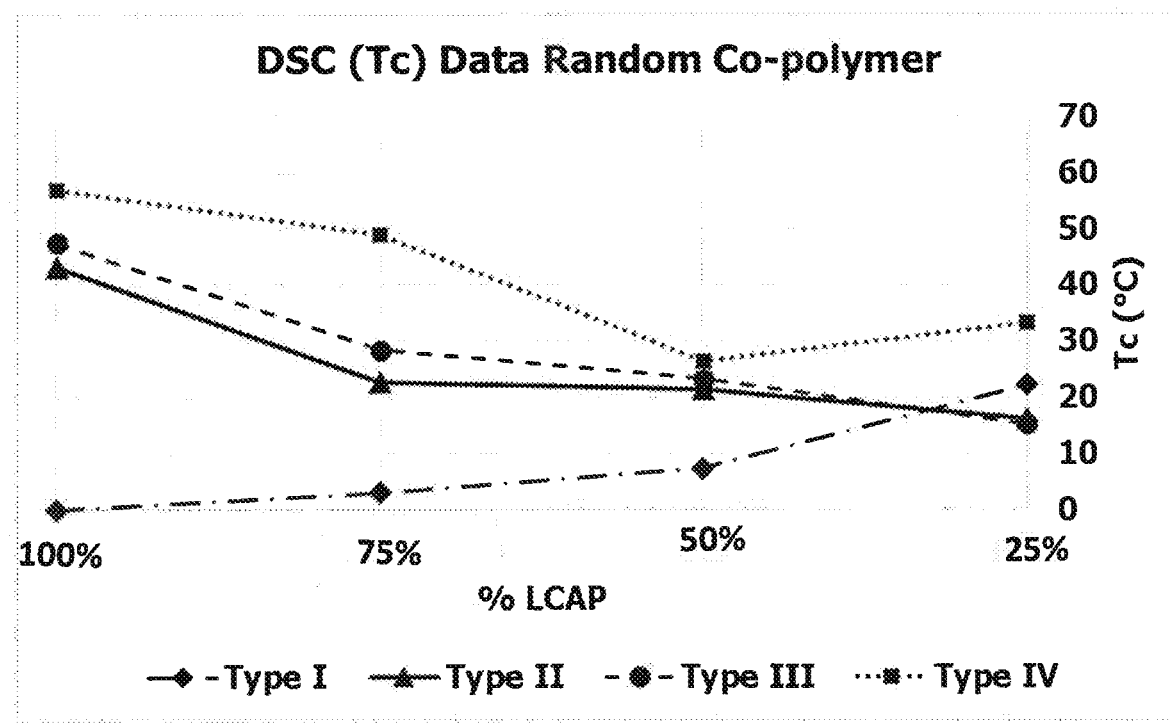
FIG. 1 is a graph showing the DSC data for the random copolymers of Examples 1-16.

It is to be understood by one of ordinary skill in the art that the present discussion is a description of exemplary embodiments only, and is not intended as limiting the broader aspects of the present invention.

Generally speaking, the present invention is directed to a thermally stable macromolecular compound, such as an alkylphenol copolymer, that can exhibit a broad spectrum of benefits, particularly when used to modify a petroleum source. By selectively controlling various aspects of the compound, such as the type, modifications or functionalities, monomers/co-monomers, and relative molar concentrations of the co-monomers, the present inventors have discovered that the resulting macromolecular compound can be tailored to provide a wide variety of beneficial properties, in particular to a petroleum composition.

In addition, the macromolecular compound, such as the alkylphenol copolymer, exhibits desired thermal properties and stability, in particular at generally low temperatures. For instance, the macromolecular compound may exhibit a generally stable and desired viscosity and self-association property. Typically, from production to end-use, these compounds may undergo temperature changes. However, the present inventors have discovered certain compounds that still exhibit the desired performance even after undergoing such temperature changes.

Generally, the effect of temperature can be assessed by conducting an oscillation temperature sweep. In particular, for the test conducted herein, a first sweep starts at 30° C. and ends at either −20° C. or an oscillation displacement of 0 (i.e., no flow point) and is conducted with a stress of 0.4 Pa at an angular frequency of 0.25 rad/s. Subsequent oscillation temperature sweeps start at 25° C. and end at either −20° C. or an oscillation displacement $\Theta$ of 0 and is conducted with a stress of 0.4 Pa at an angular frequency of 0.25 rad/s. The subsequent sweeps may allow for the determination of the effect of the temperature change on the macromolecular compound, such as an alkylphenol copolymer. In addition, the sweeps may be conducted at a non-volatile residue percentage that may vary from 5% to 30% (e.g., 5%, 7.5%, 10%, 15%, or 20%).

When conducting the oscillation temperature sweep, the macromolecular compound exhibits an oscillation displacement $\Theta$ of greater than 0 radians at a temperature of −5° C. in a first oscillation temperature sweep. The oscillation displacement $\Theta$ may be greater than 0 radians at a temperature of −10° C. in a first oscillation temperature sweep. The oscillation displacement $\Theta$ may be greater than 0 radians at a temperature of −15° C. in a first oscillation temperature sweep. The oscillation displacement $\Theta$ may be greater than 0 radians at a temperature of −20° C. in a first oscillation temperature sweep. For instance, the oscillation displacement $\Theta$ may be greater than 0 radians at a temperature of at least −25° C., such as at a temperature of at least −30° C., such as at a temperature of at least −35° C., such as at a temperature of at least −40° C. in a first oscillation temperature sweep. In addition, such oscillation displacement $\Theta$ being greater than 0 radians at the aforementioned temperatures may also be realized in a second oscillation temperature sweep. Further, such oscillation displacement being greater than 0 radians at the aforementioned temperatures may also be realized in a third oscillation temperature sweep and in some embodiments, a fourth oscillation temperature sweep.

Furthermore, while the aforementioned indicate that the oscillation displacement $\Theta$ may be greater than 0 radians, it should be understood that the oscillation displacement $\Theta$ may also be 0.1 radians or more, such as 0.2 radians or more, such as 0.3 radians or more, such as 0.4 radians or more, such as 0.5 radians or more, such as 0.6 radians or more, such as 0.7 radians or more, such as 0.8 radians or more, such as 0.9 radians or more, such as 1 radian or more, such as 1.1 radians or more, such as 1.2 radians or more, such as 1.3 radians or more, such as 1.4 radians or more at the aforementioned temperatures. In addition, the oscillation displacement $\Theta$ may be 3 radians or less, such as 2.5 radians or less, such as 2.2 radians or less, such as 2 radians or less, such as 1.9 radians or less, such as 1.8 radians or less, such as 1.7 radians or less, such as 1.6 radians or less, such as 1.5 radians or less, such as 1.4 radians or less, such as 1.3 radians or less, such as 1.2 radians or less, such as 1.1 radians or less, such as 1 radian or less at the aforementioned temperatures.

As indicated above, after a first oscillation temperature sweep, a subsequent oscillation temperature sweep may also be conducted. In this regard, the macromolecular compound may exhibit an oscillation displacement $\Theta$ in a second oscillation temperature sweep within 25% of the oscillation displacement in the first oscillation temperature sweep at a temperature of −5° C. Such oscillation displacement $\Theta$ in a second oscillation temperature sweep may be within 20%, such as within 15%, such as within 10%, such as within 5% of the oscillation displacement $\Theta$ in the first oscillation temperature sweep at a temperature of −5° C.

In addition, the macromolecular compound may exhibit an oscillation displacement $\Theta$ in a third oscillation temperature sweep within 25% of the oscillation displacement $\Theta$ in the first oscillation temperature sweep at a temperature of −5° C. In one embodiment, such oscillation displacement $\Theta$ in a third oscillation temperature sweep may be within 20%, such as within 15%, such as within 10%, such as within 5% of the oscillation displacement $\Theta$ in the first oscillation temperature sweep at a temperature of −5° C. In a further embodiment, these percentages may be realized when comparing the third oscillation temperature sweep with the second oscillation temperature sweep.

In addition, the macromolecular compound may exhibit an oscillation displacement $\Theta$ in a fourth oscillation temperature sweep within 25% of the oscillation displacement $\Theta$ in the first oscillation temperature sweep at a temperature of −5° C. In one embodiment, such oscillation displacement $\Theta$ in a fourth oscillation temperature sweep may be within 20%, such as within 15%, such as within 10%, such as within 5% of the oscillation displacement $\Theta$ in the first oscillation temperature sweep at a temperature of −5° C. In a further embodiment, these percentages may be realized when comparing the fourth oscillation temperature sweep with the second oscillation temperature sweep. In another further embodiment, these percentages may be realized when comparing the fourth oscillation temperature sweep with the third oscillation temperature sweep.

Furthermore, the aforementioned percentages are based on a comparison of the oscillation displacement $\Theta$ at a temperature of −5° C. from different oscillation temperature sweeps. However, it should be understand that such differences (i.e., percentages) in the oscillation displacement $\Theta$ may also be observed at even lower temperatures. For instance, the aforementioned percentages may be based on the oscillation displacement at a temperature of −10° C. The aforementioned percentages may be based on the oscillation displacement at a temperature of −15° C. Further, the aforementioned percentages may be based on the oscillation displacement at a temperature of −20° C. In a further embodiment, the aforementioned percentages may be based on the oscillation displacement at a temperature of −25° C. In another embodiment, the aforementioned percentages may be based on the oscillation displacement at a temperature of −30° C. In an even further embodiment, the aforementioned percentages may be based on the oscillation displacement at a temperature of −40° C.

As indicated above, the macromolecular compound can exhibit storage stability, in particular low temperature storage stability, over a period of time. Accordingly, the aforementioned rheological properties may be realized at day 1 (i.e., day of synthesis) and after day 1. For instance, the aforementioned rheological properties may be realized after at least 2 days, such as at least 3 days, such as at least 5 days, such as at least 7 days, such as at least 10 days, such as at least 14 days, such as at least 15 days, such as at least 20 days, such as at least 21 days.

In addition, the macromolecular compound disclosed herein may exhibit flowability after being stored for a sufficient period of time at −40° C. For instance, when conducting a low-temperature static stability test, the sample may be diluted originally in Aromatic 150 (A150) (~50% NVR) to a non-volatile residue percentage that may vary from 5% to 30% (e.g., 5%, 7.5%, 10%, 15% or 20%) using a solvent (e.g., xylene, toluene, or dipentene). During the test, the samples are heated to 60° C. for at least two hours before cooling to room temperature and then left to stand under static condition in a freezer with an internal temperature of −40° C. The samples may exhibit flowability for at least 2 days, such as at least 3 days, such as at least 5 days, such as at least 7 days, such as at least 10 days, such as at least 14 days, such as at least 15 days, such as at least 20 days, such as at least 21 days.

Furthermore, the macromolecular compound can function as a viscosity modifier, asphaltene dispersant, paraffin inhibitor, scale deposition inhibitor, corrosion inhibitor, ion stabilizer, pour point depressant, normal or reverse emulsion breaking agent, antifoaming agent, wettability agent, lubricating agent, non-emulsification agent, etc. The present inventors have also discovered that the macromolecular compound can be "multi-functional" in that it exhibits two or more beneficial functions (e.g., asphaltene dispersant, paraffin inhibition, and/or viscosity modifier) when used with a petroleum source. This can reduce costs and simplify operations as it allows a single material to accomplish multiple functions rather than requiring the use of two or more separate materials.

In one embodiment, for instance, the macromolecular compound, such as the alkylphenol copolymer, may act as an asphaltene dispersant. In such embodiments, the asphaltene dispersancy parameter of the compound may be relatively low, such as about 500 or less, in some embodiments about 250 or less, in some embodiments about 100 or less, in some embodiments about 50 or less, in some embodiments about 30 or less, and in some embodiments, from about 1 to about 15, as determined in substantial accordance with ASTM D7061-12 as described herein at a non-volatile residue percentage that may vary from 5% to 30% (e.g., 15%). Further, the percent asphaltene dispersancy may also be about 50% or more, in some embodiments about 70% or more, in some embodiments about 80% or more, and in some embodiments, from about 90% to 100%, as determined in substantial accordance with ASTM D7061-12 as described herein at a non-volatile residue percentage that may vary from 5% to 30% (e.g., 15%). In general, it may be desired to have a relatively low asphaltene dispersancy parameter and a generally high percent asphaltene dispersancy.

In addition to acting as an asphaltene dispersant, the macromolecular compound, such as the alkylphenol copolymer, may also function as a paraffin inhibitor. That is, the compound may function only as a paraffin inhibitor or it may simultaneously function as an asphaltene dispersant and paraffin inhibitor. In either case, when tested according to the Cold Finger method described herein, the composition can achieve a percent paraffinic wax deposition inhibition of about 50% or more, in some embodiments about 55% or more, and in some embodiments, from about 60% to about 90% for a given model oil fluid. Without intending to be limited by theory, the ability of the compound to function effectively at low temperatures is believed to be at least partially due to its ability to retain good solubility and flow properties at low temperatures. For example, the no-flow point of the compound may be relatively low, such as about −20° C. or less, in some embodiments about −30° C. or less, and in some embodiments, from about −30° C. to about −70° C., as determined in accordance with either ASTM D-7346-15 and at a non-volatile residue percentage that may vary from 5% to 30% (e.g., 5%, 7.5%, 10%, 15%, 20%). Likewise, the time to gel may be relatively high at low temperatures, such as about 500 seconds or more, in some embodiments about 600 seconds or more, and in some embodiments, from about 800 to about 14,400 seconds as determined at a temperature of −20° C. or −30° C. as determined according to the test method provided below. In addition to simply performing well at low temperatures, good properties can be maintained at a cold temperature site without risking gel formation over a broad range of temperatures.

The macromolecular compound, such as the alkylphenol copolymer, may also exhibit further beneficial properties indicative of improved performance at low temperatures. For instance, the compound may allow for a reduction in the cloud point temperature thereby indicating a reduction in the temperature at which point a sample becomes relatively cloudy and begins to solidify. In this regard, with the compound as disclosed herein, the cloud point depression (ΔCP) may be at least 0.5° C., such as at least 1° C., such as at least 1.5° C., such as at least 2° C., such as at least 2.5° C., such as at least 3° C., such as at least 3.5° C., such as at least 4° C. when determined in accordance with ASTM D-5773. The cloud point depression (ΔCP) may be 5° C. or less, such as 4.5° C. or less, such as 4° C. or less, such as 3.5° C. or less, such as 3° C. or less, such as 2.5° C. or less, such as 2° C. or less, such as 1° C. or less when determined in accordance with ASTM D-5773. Such depression may be realized at least at a compound dosage of 2000 ppm, 1000 ppm, 500 ppm, or 250 ppm.

Furthermore, the macromolecular compound, such as the alkylphenol copolymer, may also exhibit a reduced pour point thereby indicating a reduction in the temperature at which point the flow characteristics generally diminish. For instance, with the compound as disclosed herein, the pour point depression (ΔPP) may be at least 1° C., such as at least 3° C., such as at least 5° C., such as at least 8° C., such as at least 10° C., such as at least 20° C., such as at least 30° C., such as at least 50° C., such as at least 60° C., such as at least 65° C., such as at least 70° C. when determined in accordance with ASTM D-5949. The pour point depression (ΔPP) may be 100° C. or less, such as 90° C. or less, such as 80° C. or less, such as 75° C. or less, such as 70° C. or less, such as 60° C. or less, such as 50° C. or less when determined in accordance with ASTM D-5949. Such depression may be realized at least at a compound dosage of 2000 ppm, 1000 ppm, 500 ppm, or 250 ppm.

Furthermore, as indicated above, the macromolecular compound, such as the alkylphenol copolymer, can exhibit storage stability, in particular low temperature storage stability, over a period of time. Accordingly, the aforementioned properties (e.g., asphaltene dispersancy parameter, percent asphaltene dispersancy, percent paraffinic wax deposition inhibition, no-flow point, cloud point depression, and/or pour point depression) may be realized at day 1 (i.e., day of synthesis) and after day 1. For instance, the aforementioned properties may be realized after at least 2 days, such as at least 3 days, such as at least 5 days, such as at least 7 days, such as at least 10 days, such as at least 14 days, such as at least 15 days, such as at least 20 days, such as at least 21 days.

As indicated, the above-mentioned properties are exhibited by a macromolecular compound, in particular one that may be employed to modify a petroleum source. The macromolecular compound may be an oligomer, a polymer, or a mixture thereof. In one embodiment, the macromolecular compound may be an oligomer. In another embodiment, the macromolecular compound may be a polymer.

In general, the macromolecular compound may be any compound, in particular one used to modify a petroleum source. For instance, the macromolecular compound may be a polymer, such as one used to modify a petroleum source. For instance, the polymer may be an alkylphenol polymer or copolymer, an acrylate polymer or copolymer, a methacrylate polymer or copolymer, an olefin polymer or copolymer, a styrene polymer or copolymer, or a mixture thereof. In one embodiment, the polymer comprises an acrylate polymer or copolymer, a methacrylate polymer or copolymer, an olefin polymer or copolymer, a styrene polymer or copolymer, or a mixture thereof.

For instance, the polymer may include an acrylate polymer or copolymer, a methacrylate polymer or copolymer. Such a polymer may also include an acrylate co-monomer and a methacrylate co-monomer. The acrylate and/or methacrylate may be an alkyl ester of an acrylic acid and/or methacrylic acid. For instance, the alkyl ester may be a $C_1$-$C_{30}$ alkyl ester, such as a $C_{10}$-$C_{24}$ alkyl ester, such as a $C_{10}$-$C_{16}$ alkyl ester.

Monomers utilized for forming such polymers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof. In addition, as indicated above, the monomers also include alkyl esters of the aforementioned monomers. For instance, the alkyl ester may be a long chain alkyl ester and may be a $C_1$-$C_{30}$ alkyl ester, such as a $C_{10}$-$C_{24}$ alkyl ester, such as a $C_{10}$-$C_{16}$ alkyl ester.

In addition, the polymer may include an olefin polymer or copolymer. The olefin may include an ethylene or propylene and thus the polymer may be a polyethylene, a polypropylene, or a mixture thereof. Further, an olefin copolymer may include another α-olefin, such as a $C_3$-$C_{20}$ α-olefin or $C_3$-$C_{12}$ α-olefin. Specific examples of suitable α-olefins include 1-butene, 3-methyl-1-butene, 3,3-dimethyl-1-butene, 1-pentene, 1-hexene, 1-heptene, 1-octene, 1-nonene, 1-decene, and 1-dodecene. Accordingly, the copolymer may be an ethylene/α-olefin copolymer, a propylene/α-olefin copolymer, or a mixture thereof. Furthermore, the α-olefin may be substituted or unsubstituted.

The olefin copolymer may include a monomer in addition to or in lieu of the aforementioned α-olefin in conjunction with ethylene and/or propylene. For instance, the monomer may include a monomer that provides the copolymer with functionality. For instance, the monomer may provide the resulting copolymer with a carbonyl group, an amine group, a carboxyl group, or a hydroxyl group as a side functional group (rather than a terminal functional group). In one embodiment, the monomer may include a carbonyl group such that the resulting copolymer may also include such a group. In particular, the monomer may include a maleic ester, a maleic imide, or a mixture thereof. For instance, in one embodiment, the monomer may include a maleic ester such as a maleic anhydride. In this regard, the olefin polymer or copolymer includes an alpha-olefin maleic anhydride copolymer.

Further, the polymer may include a styrene polymer or copolymer. The styrene employed for forming such a polymer or copolymer may be any utilized in the art, such as α-methyl styrene, β-methyl styrene, 3- or 4-methylstyrene. In this regard, the styrene monomer employed for forming the polymer or copolymer may be substituted or unsubstituted.

The styrene copolymer may include a monomer that provides the copolymer with functionality. For instance, the monomer may provide the resulting copolymer with a carbonyl group, an amine group, a carboxyl group, or a hydroxyl group as a side functional group (rather than a terminal functional group). In one embodiment, the monomer may include a carbonyl group such that the resulting copolymer may also include such a group. In particular, the monomer may include a maleic ester, a maleic imide, or a mixture thereof. For instance, in one embodiment, the monomer may include a maleic ester such as a maleic anhydride. In this regard, the styrene polymer or copolymer includes a styrene maleic anhydride copolymer.

While the aforementioned are directed to acrylate, methacrylate, olefin, and/or styrene polymers or copolymers, it should be understood that the monomers disclosed for each respective polymer or copolymer may be copolymerized to form another copolymer. For instance, an acrylate co-monomer may be polymerized with an olefin co-monomer. Similarly, an acrylate co-monomer may be polymerized with a styrene co-monomer. In addition, the acrylate co-monomer, methacrylate co-monomer, and olefin co-monomer may be polymerized together to form a polymer. The monomers may also include other types of monomers typically employed in the art such as acrylamide monomers (e.g., methacrylamides, etc.), vinyl monomers (e.g., vinyl acetate, vinyl propionate, etc.), and the like.

In one particular embodiment, the polymer comprises an alkylphenol polymer or copolymer and in particular an alkylphenol copolymer. The alkylphenol copolymer generally includes at least one alkylphenol monomer. In general, the alkylphenol monomer includes a monomer including a phenol and an alkyl substituent, for instance para to the hydroxyl group. The alkyl may be a straight or branched $C_1$-$C_{40}$ alkyl. For instance, the alkyl may have at least 1 carbon atom, such as at least 2 carbon atoms, such as at least 4 carbon atoms, such as at least 6 carbon atoms, such as at least 8 carbon atoms, such as at least 10 carbon atoms, such as at least 12 carbon atoms, such as at least 15 carbon atoms, such as at least 18 carbon atoms, such as at least 20 carbon atoms, such as at least 22 carbon atoms, such as at least 24 carbon atoms, such as at least 26 carbon atoms. The alkyl may have 40 or less carbon atoms, such as 36 or less carbon atoms, such as 34 or less carbon atoms, such as 32 or less carbon atoms, such as 30 or less carbon atoms, such as 26 or less carbon atoms, such as 22 or less carbon atoms, such as 20 or less carbon atoms, such as 18 or less carbon atoms, such as 16 or less carbon atoms, such as 14 or less carbon atoms, such as 12 or less carbon atoms.

For instance, the alkylphenol copolymer generally has a least one of the repeating units (A) and (B) below. In one embodiment, the alkylphenol copolymer generally has both of the following repeating units (A) and (B):

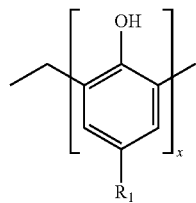

(A)

wherein, x is an integer from 1 to 200, in some embodiments from 1 to 100, in some embodiments from 1 to 50, and in some embodiments, from about 1 to about 25; and $R_1$ is a straight or branched $C_1$-$C_{15}$ alkyl, in some embodiments $C_2$-$C_{14}$ alkyl, in some embodiments $C_6$-$C_{14}$ alkyl, and in some embodiments, $C_8$-$C_{14}$ alkyl (e.g., $C_{12}$ alkyl); and

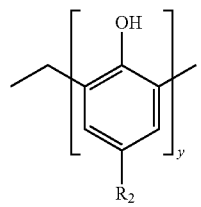

(B)

wherein, y is an integer from 2 to 200, in some embodiments from 3 to 100, in some embodiments from 4 to 50, and in some embodiments, from about 5 to about 25; and $R_2$ is a straight or branched $C_2$-$C_{40}$, in some embodiments $C_4$-$C_{40}$ alkyl, in some embodiments $C_8$-$C_{40}$, in some embodiments $C_{16}$-$C_{40}$ alkyl, in some embodiments $C_{18}$-$C_{36}$ alkyl, in some embodiments $C_{20}$-$C_{34}$ alkyl, and in some embodiments, $C_{24}$-$C_{32}$ alkyl, wherein $R_2$ is different than $R_1$. For example, the alkyl of $R_2$ typically contains 2 or more carbon atoms, in some embodiments 3 or more carbon atoms, in some embodiments 4 or more carbon atoms, and in some embodiments, 8 or more carbon atoms than the alkyl of $R_1$.

To help tailor the desired properties of the copolymer for the intended functionality, the balance between the content of the repeating units (A) and (B), as well as their respective molecular weights, may be selectively controlled. For example, the ratio of the moles of repeating unit (A) to the moles of repeating unit (B) is typically controlled within a range of from about 0.2 to about 3, in some embodiments from about 0.5 to about 2, and in some embodiments, from about 0.8 to about 1.2. The repeating unit (A) of the copolymer typically constitutes from about 20 mol. % to about 80 mol. %, in some embodiments from about 30 mol. % to about 70 mol. %, and in some embodiments, from about 40 mol. % to about 60 mol. % of the alkylphenol copolymer. Likewise, the repeating unit (B) typically constitutes from about 20 mol. % to about 80 mol. %, in some embodiments from about 30 mol. % to about 70 mol. %, and in some embodiments, from about 40 mol. % to about 60 mol. % of the alkylphenol copolymer. The number average molecular weight of the repeating unit (A) may range from about 300 to about 15,000 Daltons, in some embodiments from about 4,000 to about 12,000 Daltons, and in some embodiments, from about 4,000 to about 8,000 Daltons. The number average molecular weight of the repeating unit (B) may likewise range from about 300 to about 15,000 Daltons, in some embodiments from about 4,000 to about 12,000 Daltons, and in some embodiments, from about 4,000 to about 8,000 Daltons. The number average molecular weight of the entire copolymer may also range from about 4,000 to about 60,000 Daltons, in some embodiments from about 6,000 to about 30,000 Daltons, and in some embodiments, from about 8,000 to about 25,000 Daltons. Molecular weight may be determined using the gel permeation chromatography method described below.

Of course, it should also be understood that other repeating units or constituents may also be present in the copolymer if so desired. For instance, the copolymer may contain another repeating unit (C) that is different than the repeating units (A) and/or (B). When employed, such repeating units typically constitute no more than about 20 mol. %, in some embodiments no more than about 10 mol. %, and in some embodiments, from about 0.1 to about 5 mol. % of the alkylphenol copolymer.

In addition, it should be understood that the alkylphenol copolymer as disclosed herein may also include ortho-substituted repeating units. For instance, while the repeating units employed in synthesizing the copolymer may primarily include para-substituted repeating units, in one embodiment, the copolymer may also include some ortho-substituted repeating units wherein the alkyl group is ortho to the hydroxyl group. In this regard, the molar ratio of the para-substituted repeating units to the ortho-substituted repeating units may be within a certain range. For instance, when the ortho-substituted repeating units are utilized, the molar ratio of the para-substituted repeating units to the ortho-substituted repeating units may be about 0.1 or more, such as about 0.2 or more, such as about 0.5 or more, such as about 1 or more, such as about 1.5 or more, such as about 2 or more, such as about 3 or more, such as about 4 or more, such as about 5 or more, such as about 9 or more, such as about 10 or more, such as about 15 or more, such as about 20 or more, such as about 25 or more, such as about 50 or more, such as about 75 or more, such as about 90 or more, such as about 95 or more, such as about 99 or more. When the ortho-substituted repeating units are utilized, the molar ratio of the para-substituted repeating units to the ortho-substituted repeating units may be about 100 or less, such as about 99 or less, such as about 98 or less, such as about 95 or less, such as about 90 or less, such as about 80 or less, such as about 70 or less, such as about 60 or less, such as about 50 or less, such as about 40 or less, such as about 30 or less, such as about 20 or less, such as about 10 or less, such as about 8 or less, such as about 6 or less, such as about 5 or less, such as about 4 or less, such as about 3 or less, such as about 2.5 or less, such as about 2 or less, such as about 1 or less.

The alkylphenol copolymer may also possess any desired configuration, such as block (diblock, triblock, tetrablock, etc.), random, alternating, graft, star, etc. Nevertheless, the present inventors have discovered that block copolymers are particularly effective for use in the present invention. Without intending to be limited by theory, it is believed that the presence of block oligomer segments can allow larger regions of the repeating units (A) and/or (B) to predominate throughout the polymer chain. This results in a more ordered structure, which can improve various functions of the copolymer. For example, the ordered structure can increase the degree to which the copolymer can nucleate wax crystallization, interact with a paraffinic crystalline or asphaltene surface, thus increasing the percent wax inhibition and percent asphaltene dispersancy and decreasing the asphaltene dispersancy parameter as described below. Furthermore, the organized structure is also believed to be more stable at very low temperatures, which can enhance the ability of the resulting composition to flow at such temperatures, such as characterized by the no-flow point and static time to gel. As a result of its highly ordered structure, the polymer typically has a relatively high crystalline melting temperature, such as about 30° C. or more, and in some embodiments, from about 40° C. to about 60° C. The polymer may also have a relatively low crystallization temperature, such as about 50° C. or less, and in some embodiments, from about 10° C. to about 30° C., as well as a low glass transition temperature, such as about 60° C., and in some embodiments, from about 10° C. to about 55° C. The melting temperature, crystallization temperature, and glass transition temperature may be determined using differential scanning calorimetry (DSC), as described in more detail below. In addition, such temperatures may be realized when analyzing a neat polymer without the presence of a solvent.

The alkylphenol copolymer may be formed using any known polymerization technique as is known in the art. In one embodiment, for example, the phenol monomers used to form the copolymer are reacted with a formaldehyde source in the presence of a catalyst. Suitable formaldehyde sources may include, for instance, formaldehyde (HCHO), paraform, trioxane, alkyaldehyde, etc. Likewise, suitable phenol monomers for forming the repeating units (A) may include, for instance, butylphenol, pentylphenol, hexylphenol, dodecylphenol, nonylphenol, octylphenol, etc., as well as mixtures thereof. Suitable phenol monomers for forming the repeating units (B) may likewise include butylphenol, nonylphenol, tetracosanylphenol, pentacosanylphenol, hexacosanylphenol, heptacosanylphenol, octacosanylphenol, etc., as well as mixtures thereof. A base or acid catalyst may be employed. Examples of suitable base catalysts include sodium hydroxide, barium hydroxide, potassium hydroxide, calcium hydroxide, organic amines, sodium carbonate, and combinations thereof. Examples of suitable acid catalysts include hydrochloric acid, sulfuric acid, phosphoric acid, sulfonic acid, sulfamido acids, haloacetic acids, and combinations thereof. In particular embodiments, a sulfonic acid catalyst (e.g., p-toluene sulfonic acid or dodecylbenzenesulfonic acid) is employed. The reaction typically occurs at an elevated temperature, such as a temperature of from about 50° C. to about 180° C., and in some embodiments, from about 80° C. to about 120° C.

The manner in which the reaction occurs can depend in part on the type of polymer that is being formed. For example, when forming a random alkylphenol copolymer, the phenol monomers may be reacted with a formaldehyde source within a single reaction vessel. In such embodiments, the ratio of the total number of moles of the formaldehyde source added to the reaction vessel to the total number of moles of the phenol monomers may range from about 0.5 to about 1, and in some embodiments, from about 0.8 to about 0.95. A similar technique may be employed when forming a block copolymer. In other cases, however, it may be desirable to initially form a prepolymer prior to completing the polymerization process. In this regard, the phenol monomer used to form the repeating units (A) may be reacted with formaldehyde in a first reaction vessel and the phenol monomer used to form the repeating units (B) may be reacted with the formaldehyde source in a second reaction vessel. In such embodiments, the ratio of the total number of moles of the formaldehyde source added to the first reaction vessel to the total number of moles of the phenol monomers used to form the repeating units (A) may range from about 0.5 to about 1, and in some embodiments, from about 0.6 to about 0.85, and the ratio of the total number of moles of the formaldehyde source added to the second reaction vessel to the total number of moles of the phenol monomers used to form the repeating units (B) may range from about 0.5 to about 1, and in some embodiments, from about 0.6 to about 0.85. Once the oligomers are formed, they may then be combined together in a reaction vessel and again reacted with a formaldehyde source to complete the polymerization and formation of a block copolymer. In such embodiments, the ratio of the total number of moles of the formaldehyde source added to the reaction vessel to the total number of moles of the oligomers may range from about 0.01 to about 0.5, and in some embodiments, from about 0.05 to about 0.2.

As indicated herein, the macromolecular compound may also be an oligomer. The oligomer may include at least 2, such as at least 3, such as at least 4, such as at least 5 repeating units and may include 50 or less, such as 40 or less, such as 30 or less, such as 20 or less, such as 10 or less, such as 8 or less, such as 5 or less repeating units. For instance, the oligomer may be a short chain of repeating units of a carboxylic acid. For instance, the carboxylic acid may react to form a short chain macromolecular compound. In this regard, the carboxylic acid comprises at least one unsaturated carbon-carbon bond and in particular at least one carbon-carbon double bond. The carboxylic acid may include maleic acid, fumaric acid, or a mixture thereof. In one embodiment, the oligomer may be one formed from maleic acid. In another embodiment, the oligomer may be one formed from fumaric acid. In a further embodiment, the oligomer may be one formed from maleic acid and fumaric acid.

As indicated herein, the macromolecular compound, such as the alkylphenol copolymer, can be employed to modify a petroleum source. In this regard, the present invention, in one embodiment, is also directed to a petroleum composition comprising a petroleum source and a macromolecular compound as defined herein. The petroleum source may be a source of crude oil, another unrefined petroleum source, or a product derived therefrom, such as heating oil, fuel oil, bunker C oil, bitumen, etc.

Regardless of the particular manner in which it is formed, the macromolecular compound, such as the alkylphenol copolymer, is typically employed at a concentration of at least about 1 ppm, such as at least about 2 ppm, such as at least about 5 ppm, such as at least about 10 ppm, such as at least about 25 ppm, such as at least about 50 ppm, such as at least about 100 ppm, such as at least about 250 ppm, such as at least about 500 ppm, based on the combined weight of the macromolecular compound and the petroleum source. The compound is typically employed at a concentration of about 5,000 ppm or less, such as about 4,000 ppm or less, such as about 3,000 ppm or less, such as about 2,000 ppm or less, such as about 1,500 ppm or less, such as about 1,250 ppm or less, such as about 1,000 ppm or less, such as about 900 ppm or less, such as about 750 ppm or less, based on the combined weight of the macromolecular compound and the petroleum source. In particular, the compound is employed at a concentration of from about 1 to about 2,000 ppm, in some embodiments from about 2 to about 1,500 ppm, in some embodiments from about 5 to about 1,200 ppm, and in some embodiments, from about 10 to about 1,000 ppm, based on the combined weight of the macromolecular compound and the petroleum source.

The particular manner in which the macromolecular compound is added to a petroleum source may vary. If desired, the compound may be employed in the form of a concentrated composition that contains the compound as the primary ingredient. In other embodiments, the compound may be employed in a composition that is in the form of a dispersion or solution that contains one or more solvents in combination with the compound. Dilution may occur prior to use, or it may also occur in the field by an end user of the composition. When employed, suitable solvents may include organic solvents, such as aliphatic and/or aromatic hydrocarbons. Particularly suitable solvents include, for instance, petroleum-based solvents that include refined petroleum distillates or solvents. Refined petroleum distillates or solvents may include, for instance, aromatic compounds, such as benzene, toluene, xylene, light aromatic naphtha, heavy aromatic naphtha (HAN), kerosene, etc.; aliphatic compounds, such as pentane, hexane, heptane, octane, nonane, decane, undecane, dodecane, tridecane, tetradecane, pentadecane, hexadecane, etc.; as well as mixtures thereof. Naphtha is a petrochemical industry term describing boiling point fractions of petroleum distillate collected at different points on a distillation column. Naphtha fractions may include linear or branched or cyclic alkanes or alkenes, aromatic hydrocarbons, or fused ring aromatic compounds or mixtures of these materials. Light naphtha is a lower boiling material that is collected near the top portion of the distillation column. Medium naphtha is a higher boiling material that is collected from near the middle of the column. Finally, heavy naphtha is an even higher boiling material that is collected from near the bottom portion of the column. When solvents are employed, they typically constitute from about 30 wt. % to about 99 wt. %, in some embodiments from about 50 wt. % to about 95 wt. %, and in some embodiments, from about 60 wt. % to about 90 wt. % of the composition. Likewise, compound(s), such as described herein, may constitute from about 1 wt. % to about 70 wt. %, in some embodiments from about 5 wt. % to about 50 wt. %, and in some embodiments, from about 10 wt. % to about 40 wt. % of the composition.

In addition to a macromolecular compound, the composition may also contain one or more additional ingredients as is known in the art, such as corrosion inhibitors, surfactants, neutralizers, stabilizers, plasticizers, biocides, preservatives, etc. Suitable corrosion inhibitors may include, for instance, sulfonates, imidazolines, amines, amides, esters, as well as salts and/or polymers thereof. Examples of amine corrosion inhibitors may include n-tetradecyl amine, n-hexadecylamine, lauryl amine, myristyl amine, palmityl amine, stearyl amine, and oleyl amine, etc. When employed, an additional ingredient may be combined with the compound at any point after it is formed. For instance, an additional ingredient may be combined with the compound after it is diluted with a solvent or it may be simultaneously added as the compound is being formed. Likewise, the additional ingredients may be added at a single point in time or combined with the compound in the field to form the composition, such as in response to a certain environmental condition. As an example, one or more additional ingredients may be combined with the compound just prior to transportation or storage, or even just prior to the addition of the compound to the petroleum source, such as the crude oil.

One example of a suitable additional ingredient is a surfactant, which may be employed in an amount of from about 0.1 wt. % to about 10 wt. %, and in some embodiments, from about 0.2 wt. % to about 1 wt. % of the composition. Suitable surfactants may include nonionic surfactants, amphoteric surfactants, and/or anionic surfactants. Examples of suitable nonionic surfactants may include, for instance, alkoxylated alcohols, such as copolymers of ethylene oxide and/or propylene oxide and/or butylene oxide and epoxylated, propoxylated, and epoxylated-propoxylated compounds formed from $C_6$-$C_{40}$ alkanols. Other nonionic surfactants may also be employed, such as alkylphenol alkoxylates (e.g., nonylphenol ethoxylate), block copolymers of ethylene, propylene and butylene oxides, alkyl polyglucosides, polyalkoxylated glycerides, sorbitan esters and polyalkoxylated sorbitan esters, and alkoyl polyethylene glycol esters and diesters. Examples of suitable amphoteric surfactants may include alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, betaines, sultaines, alkyl amphoacetates and amphodiacetates, alkyl amphopropionates and amphodipropionates, dodecylbenzene sulfonic acid, and alkyliminodipropionate. Likewise, examples of suitable anionic surfactants may include alkylbenzene sulfonates, alkyldiphenoxyether sulfonates and disulfonates, napthalene sulfonates, linear and branched alkyl sulfonates, fatty alcohol sulfates, fatty alcohol ether sulfates, linear and branched alpha olefin sulfonates.

Neutralizers may also be employed in the composition if desired. For example, unreacted formaldehyde and/or unused acid catalysts (e.g., dodecylbenzenesulfonic acid) can sometimes remain present within the composition. Unreacted formaldehyde can potentially act as a crosslinking agent that causes unwanted solidification at low temperatures, while unused acid catalysts potentially precipitate as seed crystals at low temperatures. Thus, a base compound may be added to neutralize these components, such as a compound that contains one or more amine moieties (e.g., alkyl amine). Suitable alkyl amines may include monoamines (e.g., methyl amine), diamines (e.g., ethylenediamine), triamines (e.g., diethylenetriamine), etc. When employed, the neutralizer may be added in an amount of from about 0.01 wt. % to about 1 wt. %, and in some embodiments, from about 0.05 wt. % to about 0.5 wt. % of the composition.

When employed, the composition containing the macromolecular compound, such as the alkylphenol copolymer, solvent(s), and other optional components may be combined with a petroleum source in an amount of at least about 1 ppm, such as at least about 2 ppm, such as at least about 5 ppm, such as at least about 10 ppm, such as about least about 15 ppm, such as at least about 20 ppm, such as at least about 25 ppm, such as at least about 50 ppm, such as at least about 100 ppm, such as at least about 250 ppm, such as at least about 500 ppm, based on the combined weight of the composition and the petroleum source. The composition is typically employed at a concentration of about 5,000 ppm or less, such as about 4,000 ppm or less, such as about 3,000 ppm or less, such as about 2,000 ppm or less, such as about 1,500 ppm or less, such as about 1,250 ppm or less, such as about 1,000 ppm or less, such as about 900 ppm or less, such as about 750 ppm or less, based on the combined weight of the composition and the petroleum source. In particular, the composition is employed in an amount of from about 10 to about 5,000 ppm, in some embodiments from about 15 to about 1,800 ppm, and in some embodiments, from about 20 to about 1,500 ppm, based on the combined weight of the petroleum source and the composition. The composition may be added to the petroleum source in a variety of different ways to form the petroleum composition, such as during storage and/or transportation of a petroleum source. For example, the composition containing the macromolecular compound may be readily poured or pumped from a storage container or vessel into contact with a petroleum source. The composition containing the macromolecular compound can be stored within a container for at least some period of time, removed from the container, and then applied to the petroleum source. The duration of storage may vary from about 1 day to five years, such as about 2 days to 1 year, or about 1 week to 6 months, or about 2 weeks to 4 months, or about 1 to 2 months. The method of applying the composition containing the macromolecular compound to the petroleum source is not particularly limited and can be conventionally added by using available equipment, such as pipes, mixers, pumps, tanks, injection ports, etc. In some embodiments, the composition is applied to one or more subterranean hydrocarbon recovery (oil well) locations, such as downhole or on the backside using capillary string, gas lift, slip stream or other methods, at the wellhead, or at any other point downstream of the reservoir. The composition may also be employed in combination with umbilical drilling equipment.

The present invention may be better understood with reference to the following examples.

Test Methods

Differential Scanning Calorimetry (DSC):
The following equipment was used for this test:
TA Instruments DSC Q2000 with RCS90 Cooling System
TA Instruments Advantage Software with TA Instrument Explorer for instrument control
TA Instruments Universal Analysis software for data analysis
TA Instruments Tzero DSC pans and lids (aluminum)
TA Instruments Tzero Press
Microbalance Initially, 8 to 11 mg of the sample (to the nearest 0.01 mg) was weighed into a Tzero aluminum pan so that the sample made good contact with the bottom of the pan. Using forceps, the pan lid was put into place and crimped to seal. The appropriate pre-weighed Tzero reference pan was also identified in the autosampler tray, and the autosampler was programmed to load the reference pan along with the sample pan. The sample was then analyzed using the following conditions:
Purge Gas: Nitrogen
Purge Rate: 50 mL/min
Load Temperature: 40° C.
Temperature Profile: hold 3 minutes at 10° C., heat to 150° C. at a rate of 10° C./min, cool to 10° C. at a rate of 40° C./min, and hold 3 minutes at 10° C. (Cycle 1) and then heat again to 150° C. at a rate of 10° C./min (Cycle 2).

Asphaltene Dispersancy:

The effectiveness of an asphaltene dispersant may be determined in substantial accordance with ASTM D7061-12. More particularly, depending on the grade of oil, the oil sample may need to be diluted with toluene before destabilizing with heptane. The asphaltenic fluid used in this test was prepared by dissolving a bitumen into a mixture of 70 vol. % A150 fluid (Solvesso 150) and 30 vol. % Exssol D60 at a non-volatile residue ("NVR") concentration of 10%, but was not heated to ensure homogeneity or further diluted with toluene as specified by ASTM D7061-12. Five (5) samples were initially prepared by adding 1.7 milligrams of a solution having a NVR concentration of 15% to an empty vial. The sample dispersant was then diluted to a total mass of 10 grams with crude oil using an analytical balance and combined with the NVR solution to form 25-ppm active dosed samples. The resulting sample solutions were then destabilized with 10-20 grams of n-heptane. One sample was left untreated to serve as a "blank", which was the internal standard for comparing the other treated crude oil samples. Once formed, all of the samples were re-mixed by inverting them 10 times before being loaded into a Turbiscan™ tower at a temperature set point of 30° C. (with a range capability of between 4° C. and 80° C.). The instrument transmits light into the sample (wavelength of 880 nm), where it is scattered by objects in suspension, such as droplets, solid particles, bubbles, etc. After scattering, the light emerges from the sample and is detected by the instrument's detector system, which employs a mobile reading head having an NIR diode and two detectors (i.e., transmission detector and backscattering detector).

During the test, the Turbiscan™ tower measured the percent of light transmitted through the sample. The samples were scanned every two minutes over the period of 1 hour. The average percent transmission was recorded for each sample and graphed as a function of time and these values were calculated for the middle zone of the sample based on the instrument's predefined zone settings. From this graph, the integrated area under the curve was calculated and recorded as the "asphaltene dispersancy parameter." The "percent asphaltene dispersancy" relative to a blank was also determined by subtracting the area under the curve for a test sample from the area under the curve for an untreated blank, and then dividing this calculated difference by the area under the curve for the untreated blank. Generally speaking, those samples exhibiting smaller asphaltene dispersancy parameters (area under the curve) or a higher percent inhibition are considered better dispersants.

Cold Finger Evaluation of Model Oils:

Cold finger experiments were run on a F5 Multi-place cold finger (F5 Technologie GmbH, Model 0.62) using four model oil types, i.e., Model Oil 1, Model Oil 3, Model Oil 4, and Model Oil 5. More particularly, the model oils contained a mixture of a known concentration of a certain type of refined waxes dissolved in a mixture of 70 vol. % A150 fluid (Solvesso 150) and 30 vol. % Exssol D60. The exact compositions are listed in Table 1. In addition to the Model Oils of Table 1, analyses were also performed on actual crude oils (Oils 6 and 7) as indicated in Table 2.

TABLE 1

Model Oil Compositions

| Fluid | wt % Wax A | wt % Wax B | wt % Wax C | wt % Wax D | Total wt % waxes |
|---|---|---|---|---|---|
| Model Oil 1 | 5% WAKO 42-44 | 5% WAKO 66-68 | | | 10 |
| Model Oil 3 | 3% SASOL 4610 | 2% SASOL 4110 | 1% SASOL C80M | 0.1% SASOL H1 | 6.1 |
| Model Oil 4 | 5% SIGMA ALDRICH 53 | | | | 5 |
| Model Oil 5 | 5% SASOL 4610 | 5% SASOL 4110 | | | 10 |

To determine the experimental temperature conditions for both the bath temperature ($T_{oil}$) and the temperature for the finger ($T_f$), the wax appearance temperature (WAT or cloud point) of the untreated fluid was measured by differential scanning calorimetry (DSC) as described above. This onset temperature for wax precipitation was used to set $T_{oil}$, the bath temperature for heating the fluid in the cup, which was set between 0-8° C. (for Model Oils 1, 3, 4, and 5) and between 2-3° C. (for Oils 6 and 7) above the WAT, and the finger temperature was set between 10 to 20° C. below $T_{oil}$. This differential in temperature between the bath and finger (target a $\Delta T = 15°$ C. for each experiment) created a temperature gradient between the bulk fluid and the surface of the finger. The specific test conditions for all fluids are set forth below in Table 2.

TABLE 2

Cold Finger Conditions for Untreated Fluids

| Fluid | WAT (° C.) | $T_{oil}$ (° C.) | $T_f$ (° C.) | $\Delta T$ (° C.) | Avg. Blank deposit (g) | Time (hrs) |
|---|---|---|---|---|---|---|
| Model Oil 1 (MO1) | 31.9 | 35 | 20 | 15 | 2.76 | 4 |
| Model Oil 3 (MO3) | 36.6 | 36 | 21 | 15 | 0.91 | 4 |
| Model Oil 4 (MO4) | 13.5 | 17 | 7 | 10 | 1.65 | 4 |
| Model Oil 5 (MO5) | 27.8 | 31 | 16 | 15 | 1.81 | 4 |
| Oil 6 (O6) | 16 | 18 | 3 | 15 | — | 24 |
| Oil 7 (O7) | 15 | 17 | 2 | 15 | — | 24 |

To determine the final amount of material deposited onto the cold finger, the deposit was carefully removed from the cold finger cylinder and weighed. The experiments were run for a long enough period of time (e.g., greater than 4 hours) to deposit wax for an untreated sample such that the blank deposit was greater than 0.200 grams of wax. Samples were prepared by dosing the desired amount of test sample gravimetrically and mixing them with the required amount of preheated test fluids. The treated samples were conditioned in a temperature controlled oven set at 60-70° C. for a period of at least 4 hours before starting the cold finger experiment. In each experiment, an untreated blank was run concomitantly with the fluids treated with the experimental paraffin inhibitor. Based on the test procedure performed above, the paraffinic wax inhibition or percent reduction for a given test sample may then be determined by subtracting the weight of wax deposited by the test sample from the weight of wax deposited by the untreated blank, and then dividing this calculated difference by the weight of wax deposited by the untreated blank.

Rheological Evaluation:

Rheology experiments were performed on a TA Discovery HR-1 stress controlled rheometer using a parallel plate geometry with a 40 mm diameter stainless steel upper plate and a Peltier-cooled bottom plate. To minimize solvent loss during experiments, the solvent trap of the top plate was filled with the same solvent used to dissolve the sample and this trap was used in concert with a solvent trap cover that was placed over a Peltier stage. The Peltier solvent trap was equipped with gas inlet fittings and the geometry was swept with a slow stream of nitrogen to minimize water condensation during experiments performed below room temperature. Two methods were used to assess the flow properties of product formulations in A150 fluid solutions at a non-volatile residue ("NVR") concentration of 15%. The no-flow-point ("NFP") method was used to determine the temperature at which the sample no longer flowed when a controlled stress is applied to the sample while the temperature of the sample is decreased. The time-to-gel ("TTG") method was used to determine the time that it takes a sample to gel when held under static conditions at either −20° C. or −30° C. These test methods are described in more detail below.

No Flow Point:

To perform this test, the Peltier stage was equilibrated to 40° C., the sample was loaded into a trim gap of 350 μm, and the sample was trimmed at a gap of 300 μm by drawing excess sample into a pipette. The sample was then conditioned by preheating to 80° C., holding for 600 seconds, and then initiating a preconditioning step in which the sample was sheared at a rate of 0.1 s$^{-1}$ for 150 seconds. The sample was then cooled to either 10° C. or 30° C. and then the oscillation temperature sweep was executed. Measurements were taken at 3° C. temperature steps with a stress of 0.4 Pa and an angular frequency of 0.25 rad/s. The reported value for the rheological no-flow-point was the temperature at which the oscillation displacement reached zero.

Oscillatory Temperature Sweeps:

To perform this test, rheology experiments were carried out on a DHR-1 stress controlled rheometer (TA Instruments) using a parallel plate with a 40 mm diameter stainless steel upper plate and a Peltier-cooled bottom plate. All samples were diluted in A150 solutions at a non-volatile residue concentration of 15% or 7.5%. The sample was loaded into a trimmed gap of 300 μm by drawing excess sample into a pipette and then conditioned by preheating to 50° C., holding for 600 seconds, and then initiating a preconditioning step in which the sample was sheared at a rate of 0.1 s$^{-1}$ for 150 seconds. The sample was then cooled to 30° C. and swept to an end point of −20° C. or to the end-point when the oscillation displacement reached zero. At the end of each sweep, the sample was heated back to 25° C. to repeat the cycling process down to −20° C. Measurements were taken at 3° C. temperature steps with a stress of 0.4 Pa and an angular frequency of 0.25 rad/s.

Time to Gel (TTG):

To perform this test, the Peltier stage was equilibrated to 40° C., the sample was loaded into a trim gap of 350 μm and the sample was trimmed at a gap of 300 μm by drawing excess sample into a pipette. The sample was then conditioned by preheating to 80° C., holding for 600 seconds, and then initiating a preconditioning step in which the sample was sheared at a rate of 0.1 s$^{-1}$ for 150 seconds. Depending on the TTG method, the sample was then cooled to either −20° C. or −30° C., and then the oscillation time-to-gel was executed. Measurements were taken with a stress of 0.4 Pa and an angular frequency of 0.25 rad/s for a maximum duration of 14,400 seconds (4 hours). The reported value for the time-to-gel was the time for the loss modulus (G') and storage modulus (G") to crossover, with the exception for samples that pass the 4 hour window, which were reported as >4 hrs.

Gel Permeation Chromatography (GPC):
The following equipment was used during this test:
Liquid Chromatograph: Agilent 1260 Series Liquid Chromatograph equipped with an Ultraviolet and/or a Refractive Index detector(s), auto-sampler and auto-injector
Cirrus GPC/SEC software v. 3.4.1, Chemstation OpenLab v. C.01.05
In-Line Pre-Column Filter Kit; SSI (Alltech): Filter housing, 35-0148, Replacement Filters, 2.0 μm, 05-0154
Chromatography Columns (Agilent):

| Pore Size(°A) | Dimensions |
|---|---|
| 500 | 300 mm × 7.5 mm × 5 μm |
| $1 \times 10^3$ | 300 mm × 7.5 mm × 5 μm |
| $1 \times 10^4$ | 300 mm × 7.5 mm × 5 μm |
| $1 \times 10^5$ | 300 mm × 7.5 mm × 5 μm |

2 mL glass vials with Teflon lined cap (Hewlett-Packard 5181-3400)
Scintillation Vials: 20 mL, Wheaton 12-986546
Pipets: disposable
50 mL amber dropping bottle
The chromatograph operating parameters were also as follows:
Mobile Phase: 99/1 Tetrahydrofuran/Methanol
Flow: 1.2 mL/min
Injection Volume: 50 μL
UV Detector Wavelength: 280 nm (Samples), 254 nm (Standards)
Peak Threshold: System dependent-high enough to pick up the peaks but not so low that noise is detected
Peak Width: System dependent
Samples: Integration on 10 minutes, processing started before the sample baseline begins to rise (~10.1 minutes). The end processing time is the time of the baseline minimum just before phenol elutes. Phenol is injected in one of the standard sets and is used as a marker, even for samples that do not contain phenol.

For UV detection, 0.01 g (±0.01) of the sample was weighed into a 20 mL scintillation vial. The vial was filled with 4 mL of the 50 ppm sulfur in a tetrahydrofuran (THF) solution and dissolved. If the sample dissolved completely, it was transferred to a HPLC vial using a dropper pipet. If the sample appears cloudy, it was filtered through a 0.45 μM PTFE syringe filter before being added to the HPLC vial. For RI detection, 0.05 (±0.01) of the sample was weighed into a 20 mL scintillation vial. The vial was filled with 4 mL of the mobile phase currently in use. If the sample dissolved completely, it was transferred to a HPLC vial using a dropper pipet. If the sample appeared cloudy, it was filtered through a 0.45 μM PTFE syringe filter before being added to the HPLC vial. Depending on the reliability of the pump, the standard solutions may be run as often as once every month. With the Cirrus software, each sample has a "Flow Rate Correction Factor", which compared the retention time of the sulfur from the sample run to the sulfur retention time from when the calibration table was created (for UV). If the times matched exactly, the factor was one. If the factor changed significantly, the flow was checked to ensure that the method flow was being obtained. If the flow was correct, the calibration standards were run to update the calibration table. Slight changes in the retention time of the sulfur may occur over time as the columns age, and sulfur shift in the UV detection indicates that recalibration should be performed for both detectors.

Cloud Point (CP) and Pour Point (PP):
The following equipment was used for this test:
PhaseTechnology ASL-70Xi Autosampler Analyzer
The Phase Technology ASL-70Xi Autosampler Analyzer system is used to determine the cloud point (ASTM D5773) and pour point (ASTM D5949) of lube oils, fuels, and waxy paraffinic solutions. The cloud point and pour point were determined by following the ASTM methods developed and described for each test.

The cloud point and pour point tests are used to assess the ability of a sample to interact with the paraffinic components of a wax burdened fluid. The performance of any one sample is revealed by the measured depression of the both the cloud point and pour point temperature relative to a blank untreated sample. Furthermore, a dose-response over a range of concentrations can provide additional evidence of the magnitude of the interaction between the sample and the paraffin in solution. Samples were prepared by dosing the desired amount of test sample gravimetrically from 15% NVR stock solutions in A150 and mixing them with the required amount of preheated test fluids. The treated samples were conditioned in a temperature controlled oven set at 60-70° C. for a period of at least 4 hours before starting the cloud point and pour point tests. In each test, an untreated blank was run concomitantly with the test fluids treated with the experimental sample. All samples were compared against the average cloud point and pour point values for the untreated fluid. Based on the test procedure performed above, the cloud point depression (ΔCP) and pour point depression (ΔPP) for a given test sample may then be determined by subtracting the measured value of the test sample from the running average of the untreated blank.

Monomer Designations

For purposes of these Examples, the term "Type A" or "A-Type" monomer refers to para-dodecyl phenol ("PDDP") and the term "Type B" or "B-Type" monomer refers to a long-chain alkyl phenol ("LCAP"), i.e., $C_{16-18}$ alkyl phenol ("Type I"), $C_{24-28}$ alkyl phenol ("Type II"), $C_{26-28}$ alkyl phenol ("Type III"), and $C_{30-40}$ alkyl phenol ("Type IV").

Example 1

A polymer was formed from a Type I LCAP monomer resulting in a homopolymer of LCAP. Type I LCAP was loaded into a round bottom flask with 0.002 molar equivalents of dodecyl-benzyl-sulfonic acid and heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

Example 2

A polymer was formed according to the procedure of Example 1, except that Example 2 used Type II LCAP and required 0.06 molar equivalents of additional 50% aq. formaldehyde to meet the target molecular weight.

Example 3

A polymer was formed according to the procedure of Example 1, except that Example 3 used Type III LCAP and required 0.12 molar equivalents of additional 50% aq. formaldehyde to meet the target molecular weight.

Example 4

A polymer was formed according to the procedure of Example 1, except that Example 4 used Type IV LCAP and required 0.20 molar equivalents of additional 50% aq. formaldehyde to meet the target molecular weight.

Example 5

A polymer was formed from a combined mole ratio of 75:25 LCAP to Type A monomer resulting in a random copolymer of LCAP and Type A monomer. 0.75 molar equivalents of Type I LCAP was loaded into a round bottom flask with 0.25 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

Example 6

A polymer was formed according to the procedure of Example 5, except that Example 6 used Type II LCAP and required 0.06 molar equivalents of additional 50% aq. formaldehyde to meet the target molecular weight.

Example 7

A polymer was formed according to the procedure of Example 5, except that Example 7 used Type III LCAP and required 0.10 molar equivalents of additional 50% aq. formaldehyde to meet the target molecular weight.

Example 8

A polymer was formed according to the procedure of Example 5, except that Example 8 used Type IV LCAP, required 0.17 molar equivalents of additional 50% aq. formaldehyde to meet the target molecular weight.

Example 9

A polymer was formed from a combined mole ratio of 50:50 LCAP to Type A monomer resulting in a random copolymer of LCAP and Type A monomer. 0.5 molar equivalents of Type I LCAP was loaded into a round bottom flask with 0.5 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

Example 10

A polymer was formed according to the procedure of Example 9, except that Example 10 used Type II LCAP and required 0.13 molar equivalents of additional 50% aq. formaldehyde to meet the target molecular weight.

Example 11

A polymer was formed according to the procedure of Example 9, except that Example 11 used Type III LCAP and required 0.13 molar equivalents of additional 50% aq. formaldehyde to meet the target molecular weight.

Example 12

A polymer was formed according to the procedure of Example 9, except that Example 12 used Type IV LCAP and required 0.27 molar equivalents of additional 50% aq. formaldehyde to meet the target molecular weight.

Example 13

A polymer was formed from a combined mole ratio of 25:75 LCAP to Type A monomer resulting in a random copolymer of LCAP and Type A monomer. 0.25 molar equivalents of Type I LCAP was loaded into a round bottom flask with 0.75 molar equivalents of Type A monomer and 0.002 molar equivalents of dodecyl-benzyl-sulfonic acid, and then heated to a temperature from about 80° C. to about 120° C. 0.90 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by subsequent additions of 50% aq. formaldehyde. The reaction flask was then fitted with a Dean-Stark trap and the final reaction temperature was set to 140° C. to distill off all water.

Example 14

A polymer was formed according to the procedure of Example 13, except that Example 14 used Type II LCAP and required 0.29 molar equivalents of additional 50% aq. formaldehyde to meet the target molecular weight.

Example 15

A polymer was formed according to the procedure of Example 13, except that Example 15 used Type III LCAP and required 0.19 molar equivalents of additional 50% aq. formaldehyde to meet the target molecular weight.

Example 16

A polymer was formed according to the procedure of Example 13, except that Example 16 used Type IV LCAP and required 0.16 molar equivalents of additional 50% aq. formaldehyde to meet the target molecular weight.

Example 17

A polymer was formed from a combined mole ratio of 75:25 LCAP to Type A monomer oligomers resulting in a block co-polymer of LCAP and Type A monomer. A feedstock of Type A oligomer was made for the purposes of loading into future batches. Type A monomer was loaded into a round bottom flask with 0.002 molar equivalents of dodecyl-benzyl-sulfonic acid and then heated to a temperature from about 80° C. to about 120° C. 50% aqueous formaldehyde was loaded over 30 minutes, amounting to 0.75 molar equivalents of formaldehyde to Type A monomer, and the reaction was performed at a temperature from about 80° C. to about 120° C. under reflux. Using the GPC method to track molecular weight progression, the targeted molecular weight was achieved by post additions of 0.02 molar equivalents of 50% aq. formaldehyde. The reaction flask was then fitted with a Dean-Stark trap and the final reaction temperature was set to 140° C. to distill off all water. The Type A oligomer was set aside and another round bottom flask was loaded with 0.75 molar equivalents of Type II LCAP and 0.002 molar equivalents of dodecyl-benzyl-sulfonic acid and then heated to a temperature from about 80° C. to about 120° C. 0.75 molar equivalents of 50% aqueous formaldehyde was loaded over 30 minutes and the reaction was performed at a temperature from about 80° C. to about 120° C. under reflux. Using the GPC method to track molecular weight progression, the targeted molecular weight was achieved by post additions of 0.02 molar equivalents of 50% aq. formaldehyde. The final reaction temperature was then set to 140° C. to distill off all water. 0.25 molar equivalents of Type A oligomer was then loaded into the round bottom flask containing the 0.75 molar equivalents of Type II LCAP oligomer. Multiple additions of 50% aqueous formaldehyde were loaded until the targeted molecular weight was achieved. This example took 0.32 molar equivalents to reach the target molecular weight. The temperature was then set to 140° C. to distill off all water.

Example 18

A polymer was formed according to the procedure of Example 17, except that Example 18 used Type III LCAP and required 0.22 molar equivalents of additional 50% aq. formaldehyde to meet the target molecular weight.

Example 19

A polymer was formed according to the procedure of Example 17, except that Example 19 used Type IV LCAP and required 0.03 molar equivalents of additional 50% aq. formaldehyde to meet the target molecular weight.

Example 20

A polymer was formed according to the procedure of Example 17, except that Example 20 used 50:50 Type II LCAP to Type A monomer, and required 0.10 molar equivalents of additional 50% aq. formaldehyde to meet the target molecular weight.

Example 21

A polymer was formed according to the procedure of Example 17, except that Example 21 used 50:50 Type III LCAP to Type A monomer, and required 0.27 molar equivalents of additional 50% aq. formaldehyde to meet the target molecular weight.

Example 22

A polymer was formed according to the procedure of Example 17, except that Example 22 used 50:50 Type IV LCAP to Type A monomer, and required 0.08 molar equivalents of additional 50% aq. formaldehyde to meet the target molecular weight.

Example 23

A polymer was formed according to the procedure of Example 17, except that Example 23 used 25:75 Type II LCAP to Type A monomer, and required 0.13 molar equivalents of additional 50% aq. formaldehyde to meet the target molecular weight.

Example 24

A polymer was formed according to the procedure of Example 17, except that Example 24 used 25:75 Type III LCAP to Type A monomer, and required 0.17 molar equivalents of additional 50% aq. formaldehyde to meet the target molecular weight.

Example 25

A polymer was formed according to the procedure of Example 17, except that Example 25 used 25:75 Type IV LCAP to Type A monomer, and required 0.23 molar equivalents of additional 50% aq. formaldehyde to meet the target molecular weight.

Figure 2:
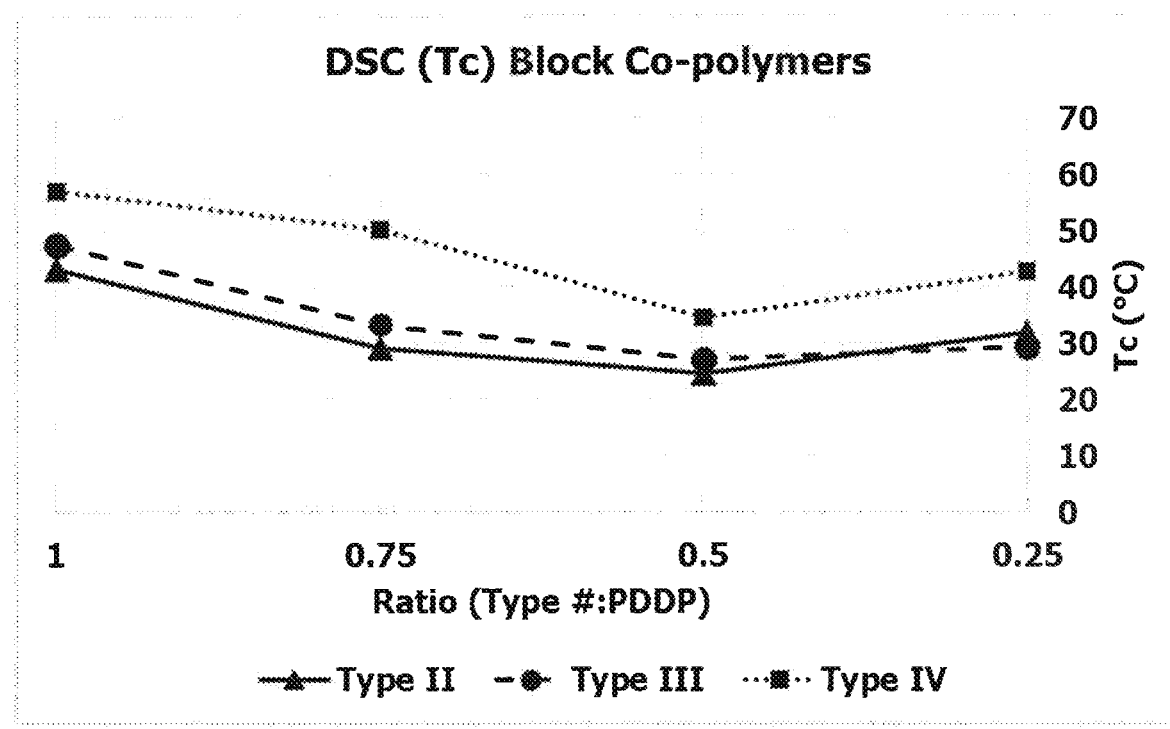
FIG. 2 is a graph showing the DSC data for the block copolymers of Examples 17-25.

A summary of the samples prepared in Examples 1-25 is provided below in Table 3 and also shown graphically in FIGS. 1-2.

TABLE 3

| Example | Type | Ratio | Polymer Type | DSC Tg [° C.] | MW (Da) |
| --- | --- | --- | --- | --- | --- |
| 1 | Type I | 100 | Random | 0 | 12117 |
| 2 | Type II | 100 | Random | 43.42 | 16637 |
| 3 | Type III | 100 | Random | 47.62 | 18602 |
| 4 | Type IV | 100 | Random | 57.18 | 18597 |
| 5 | Type I | 75 | Random | 3.08 | 14168 |
| 6 | Type II | 75 | Random | 22.91 | 14260 |
| 7 | Type III | 75 | Random | 28.64 | 15109 |
| 8 | Type IV | 75 | Random | 49.03 | 18671 |
| 9 | Type I | 50 | Random | 7.36 | 10749 |
| 10 | Type II | 50 | Random | 21.37 | 13838 |
| 11 | Type III | 50 | Random | 23.32 | 13822 |
| 12 | Type IV | 50 | Random | 26.56 | 15476 |
| 13 | Type I | 25 | Random | 22.35 | 10490 |
| 14 | Type II | 25 | Random | 16.09 | 11809 |
| 15 | Type III | 25 | Random | 15.25 | 11398 |
| 16 | Type IV | 25 | Random | 33.39 | 10440 |
| 17 | Type II | 75 | Block | 29.35 | 13624 |
| 18 | Type III | 75 | Block | 33.47 | 17653 |
| 19 | Type IV | 75 | Block | 50.54 | 16425 |
| 20 | Type II | 50 | Block | 34.59 | 11711 |
| 21 | Type III | 50 | Block | 27.35 | 14732 |
| 22 | Type IV | 50 | Block | 34.84 | 16708 |
| 23 | Type II | 25 | Block | 32.01 | 10587 |
| 24 | Type III | 25 | Block | 29.48 | 13613 |
| 25 | Type IV | 25 | Block | 43.01 | 11636 |

The DSC thermograms of the polymers listed in Table 3 are absent of any noticeable glass transition but are instead dominated by a rather large exothermic transition on the cooling cycle. The large exotherm in all of the samples is consistent with the crystallization of the long chain alkyl-sidechains of the Type B monomer. The observed reduction of crystallization is further consistent with the dilution that occurs going down the series of 75%, 50%, and 25% content for the long chain alkyl-sidechains of the Type B monomer by the addition of Type A monomer.

Once formed, the samples of Examples 2-4, 6-8, 10-12, and 14-25 were each diluted with a hydrocarbon solvent (A150 fluid) to form a composition containing 15 wt. % of the respective random or block copolymer. These compositions were then dosed at a concentration of 25 ppm and tested for asphaltene dispersancy as described above. The results are set forth below in Table 4.

TABLE 4

| Example | B-TYPE | % B-TYPE | P-TYPE | Area Under Curve | % Asphaltene Dispersancy |
|---|---|---|---|---|---|
| 2 | TYPE II | 100% | random | 229.14 | 75.6% |
| 3 | TYPE III | 100% | random | 402.63 | 57.1% |
| 4 | TYPE IV | 100% | random | 917.06 | 2.3% |
| BLANK | | | | 938.42 | — |
| 6 | TYPE II | 75% | random | 136.11 | 86.5% |
| 7 | TYPE III | 75% | random | 235.62 | 76.6% |
| 8 | TYPE IV | 75% | random | 245.94 | 75.6% |
| BLANK | | | | 1009.00 | — |
| 10 | TYPE II | 50% | random | 7.26 | 99.2% |
| 11 | TYPE III | 50% | random | 39.60 | 95.9% |
| 12 | TYPE IV | 50% | random | 31.72 | 96.7% |
| BLANK | | | | 961.65 | — |
| 14 | TYPE II | 25% | random | 4.12 | 99.6% |
| 15 | TYPE III | 25% | random | 3.89 | 99.6% |
| 16 | TYPE IV | 25% | random | 2.93 | 99.7% |
| BLANK | | | | 1038.09 | — |
| 17 | TYPE II | 75% | block | 80.68 | 90.4% |
| 18 | TYPE III | 75% | block | 111.63 | 86.7% |
| 19 | TYPE IV | 75% | block | 146.83 | 82.5% |
| BLANK | | | | 837.96 | — |
| 20 | TYPE II | 50% | block | 7.55 | 99.2% |
| 21 | TYPE III | 50% | block | 6.80 | 99.2% |
| 22 | TYPE IV | 50% | block | 10.26 | 98.9% |
| BLANK | | | | 904.06 | — |
| 23 | TYPE II | 25% | block | 9.49 | 99.1% |
| 24 | TYPE III | 25% | block | 9.65 | 99.1% |
| 25 | TYPE IV | 25% | block | 8.54 | 99.2% |
| BLANK | | | | 1092.88 | — |

The samples of Examples 1-25 were also diluted with a hydrocarbon solvent (A150 fluid) to form a composition containing about 15 wt. % of the respective random or block copolymer, and then dosed at a concentration of 1,000 ppm into each of the model oil fluids listed in Table 2. The Cold Finger paraffin inhibition was tested as set forth herein. In an effort to normalize the performance, a scoring system was also employed wherein any one additive is assigned three (3) points for reducing the wax deposit by at least 40% otherwise the additive is assigned one (1) point for failing to meet the 40% wax reduction metric. The results are set forth below in Tables 5-8.

TABLE 5

Cold Finger - MO1 Fluid

| Example | B-TYPE | % B-TYPE | POLYMER-TYPE | % reduction | Dose ppm | Score |
|---|---|---|---|---|---|---|
| 1 | TYPE I | 100% | random | 12% | 1000 | 1 |
| 2 | TYPE II | 100% | random | 69% | 1000 | 3 |
| 3 | TYPE III | 100% | random | 81% | 1000 | 3 |
| 4 | TYPE IV | 100% | random | 55% | 1000 | 3 |
| 5 | TYPE I | 75% | random | 1% | 1000 | 1 |

TABLE 5-continued

Cold Finger - MO1 Fluid

| Example | B-TYPE | % B-TYPE | POLYMER-TYPE | % reduction | Dose ppm | Score |
|---|---|---|---|---|---|---|
| 6 | TYPE II | 75% | random | 30% | 1000 | 1 |
| 7 | TYPE III | 75% | random | 95% | 1000 | 3 |
| 8 | TYPE IV | 75% | random | 54% | 1000 | 3 |
| 9 | TYPE I | 50% | random | 21% | 1000 | 1 |
| 10 | TYPE II | 50% | random | 3% | 1000 | 1 |
| 11 | TYPE III | 50% | random | 26% | 1000 | 1 |
| 12 | TYPE IV | 50% | random | 49% | 1000 | 3 |
| 13 | TYPE I | 25% | random | 22% | 1000 | 1 |
| 14 | TYPE II | 25% | random | 8% | 1000 | 1 |
| 15 | TYPE III | 25% | random | 23% | 1000 | 1 |
| 16 | TYPE IV | 25% | random | 23% | 1000 | 1 |
| 17 | TYPE II | 75% | block | 79% | 1000 | 3 |
| 18 | TYPE III | 75% | block | 75% | 1000 | 3 |
| 19 | TYPE IV | 75% | block | 80% | 1000 | 3 |
| 20 | TYPE II | 50% | block | 36% | 1000 | 1 |
| 20 | TYPE II | 50% | block | 66% | 1000 | 3 |
| 20 | TYPE II | 50% | block | 60% | 1000 | 3 |
| 20 | TYPE II | 50% | block | 50% | 1000 | 3 |
| 21 | TYPE III | 50% | block | 54% | 1000 | 3 |
| 22 | TYPE IV | 50% | block | 84% | 1000 | 3 |
| 23 | TYPE II | 25% | block | 73% | 1000 | 3 |
| 24 | TYPE III | 25% | block | 55% | 1000 | 3 |
| 25 | TYPE IV | 25% | block | 77% | 1000 | 3 |

TABLE 6

Cold Finger - MO3 Fluid

| Example | B-TYPE | % B-TYPE | POLYMER-TYPE | % reduction | Dose ppm | Score |
|---|---|---|---|---|---|---|
| 1 | TYPE I | 100% | random | 23% | 1000 | 1 |
| 2 | TYPE II | 100% | random | 74% | 1000 | 3 |
| 3 | TYPE III | 100% | random | 86% | 1000 | 3 |
| 4 | TYPE IV | 100% | random | 79% | 1000 | 3 |
| 5 | TYPE I | 75% | random | 4% | 1000 | 1 |
| 6 | TYPE II | 75% | random | 68% | 1000 | 3 |
| 7 | TYPE III | 75% | random | 76% | 1000 | 3 |
| 8 | TYPE IV | 75% | random | 81% | 1000 | 3 |
| 9 | TYPE I | 50% | random | 2% | 1000 | 1 |
| 10 | TYPE II | 50% | random | 37% | 1000 | 1 |
| 11 | TYPE III | 50% | random | 29% | 1000 | 1 |
| 12 | TYPE IV | 50% | random | 76% | 1000 | 3 |
| 13 | TYPE I | 25% | random | 4% | 1000 | 1 |
| 14 | TYPE II | 25% | random | 8% | 1000 | 1 |
| 15 | TYPE III | 25% | random | 16% | 1000 | 1 |
| 16 | TYPE IV | 25% | random | 56% | 1000 | 3 |
| 17 | TYPE II | 75% | block | 73% | 1000 | 3 |
| 18 | TYPE III | 75% | block | 69% | 1000 | 3 |
| 19 | TYPE IV | 75% | block | 81% | 1000 | 3 |
| 20 | TYPE II | 50% | block | 66% | 1000 | 3 |
| 21 | TYPE III | 50% | block | 55% | 1000 | 3 |
| 22 | TYPE IV | 50% | block | 76% | 1000 | 3 |
| 23 | TYPE II | 25% | block | 52% | 1000 | 3 |
| 24 | TYPE III | 25% | block | 52% | 1000 | 3 |
| 25 | TYPE IV | 25% | block | 79% | 1000 | 3 |

TABLE 7

Cold Finger - MO4 Fluid

| Example | B-TYPE | % B-TYPE | POLYMER-TYPE | % reduction | Dose ppm | Score |
|---|---|---|---|---|---|---|
| 1 | TYPE I | 100% | random | 6% | 1000 | 1 |
| 2 | TYPE II | 100% | random | 76% | 1000 | 3 |
| 3 | TYPE III | 100% | random | 69% | 1000 | 3 |
| 4 | TYPE IV | 100% | random | 14% | 1000 | 1 |
| 5 | TYPE I | 75% | random | −1% | 1000 | 1 |
| 6 | TYPE II | 75% | random | 67% | 1000 | 3 |

TABLE 7-continued

Cold Finger - MO4 Fluid

| Example | B-TYPE | % B-TYPE | POLYMER-TYPE | % reduction | Dose ppm | Score |
|---|---|---|---|---|---|---|
| 7 | TYPE III | 75% | random | 64% | 1000 | 3 |
| 8 | TYPE IV | 75% | random | 16% | 1000 | 1 |
| 9 | TYPE I | 50% | random | 10% | 1000 | 1 |
| 10 | TYPE II | 50% | random | 57% | 1000 | 3 |
| 11 | TYPE III | 50% | random | 58% | 1000 | 3 |
| 12 | TYPE IV | 50% | random | 36% | 1000 | 1 |
| 13 | TYPE I | 25% | random | −1% | 1000 | 1 |
| 14 | TYPE II | 25% | random | 27% | 1000 | 1 |
| 15 | TYPE III | 25% | random | 22% | 1000 | 1 |
| 16 | TYPE IV | 25% | random | 4% | 1000 | 1 |
| 17 | TYPE II | 75% | block | 70% | 1000 | 3 |
| 18 | TYPE III | 75% | block | 71% | 1000 | 3 |
| 19 | TYPE IV | 75% | block | 18% | 1000 | 1 |
| 20 | TYPE II | 50% | block | 50% | 1000 | 3 |
| 21 | TYPE III | 50% | block | 60% | 1000 | 3 |
| 22 | TYPE IV | 50% | block | 37% | 1000 | 1 |
| 23 | TYPE II | 25% | block | 17% | 1000 | 1 |
| 24 | TYPE III | 25% | block | 48% | 1000 | 3 |
| 25 | TYPE IV | 25% | block | 33% | 1000 | 1 |

TABLE 8

Cold Finger - MO5 Fluid

| Example | B-TYPE | % B-TYPE | POLYMER-TYPE | % reduction | Dose ppm | Score |
|---|---|---|---|---|---|---|
| 1 | TYPE I | 100% | random | 10% | 1000 | 1 |
| 2 | TYPE II | 100% | random | 57% | 1000 | 3 |
| 3 | TYPE III | 100% | random | 70% | 1000 | 3 |
| 4 | TYPE IV | 100% | random | 65% | 1000 | 3 |
| 5 | TYPE I | 75% | random | 18% | 1000 | 1 |
| 6 | TYPE II | 75% | random | 41% | 1000 | 3 |
| 7 | TYPE III | 75% | random | 61% | 1000 | 3 |
| 8 | TYPE IV | 75% | random | 67% | 1000 | 3 |
| 9 | TYPE I | 50% | random | 15% | 1000 | 1 |
| 10 | TYPE II | 50% | random | 24% | 1000 | 1 |
| 11 | TYPE III | 50% | random | 31% | 1000 | 1 |
| 12 | TYPE IV | 50% | random | 62% | 1000 | 3 |
| 13 | TYPE I | 25% | random | −7% | 1000 | 1 |
| 14 | TYPE II | 25% | random | −14% | 1000 | 1 |
| 15 | TYPE III | 25% | random | −139% | 1000 | 1 |
| 16 | TYPE IV | 25% | random | 4% | 1000 | 1 |
| 17 | TYPE II | 75% | block | 65% | 1000 | 3 |
| 18 | TYPE III | 75% | block | 70% | 1000 | 3 |
| 19 | TYPE IV | 75% | block | 53% | 1000 | 3 |
| 20 | TYPE II | 50% | block | 59% | 1000 | 3 |
| 21 | TYPE III | 50% | block | 55% | 1000 | 3 |
| 22 | TYPE IV | 50% | block | 61% | 1000 | 3 |
| 23 | TYPE II | 25% | block | 40% | 1000 | 3 |
| 24 | TYPE III | 25% | block | 43% | 1000 | 3 |
| 25 | TYPE IV | 25% | block | 46% | 1000 | 3 |

Figure 3:
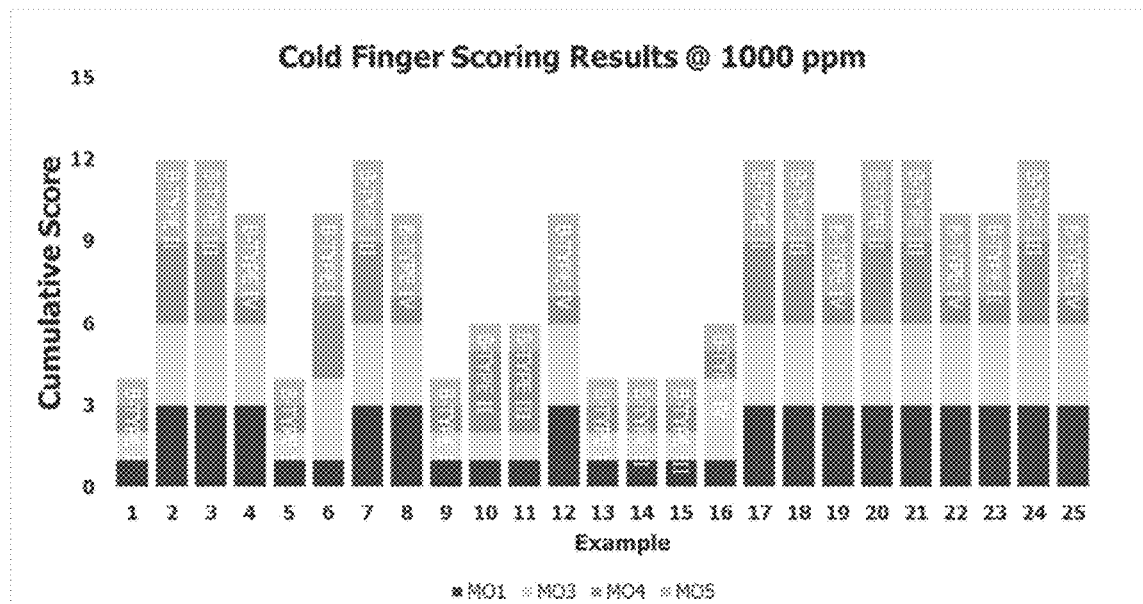
FIG. 3 is a graph showing the cumulative scoring results (at 1,000 ppm) of Cold Finger testing for the samples of Examples 1-25.
Figure 4:
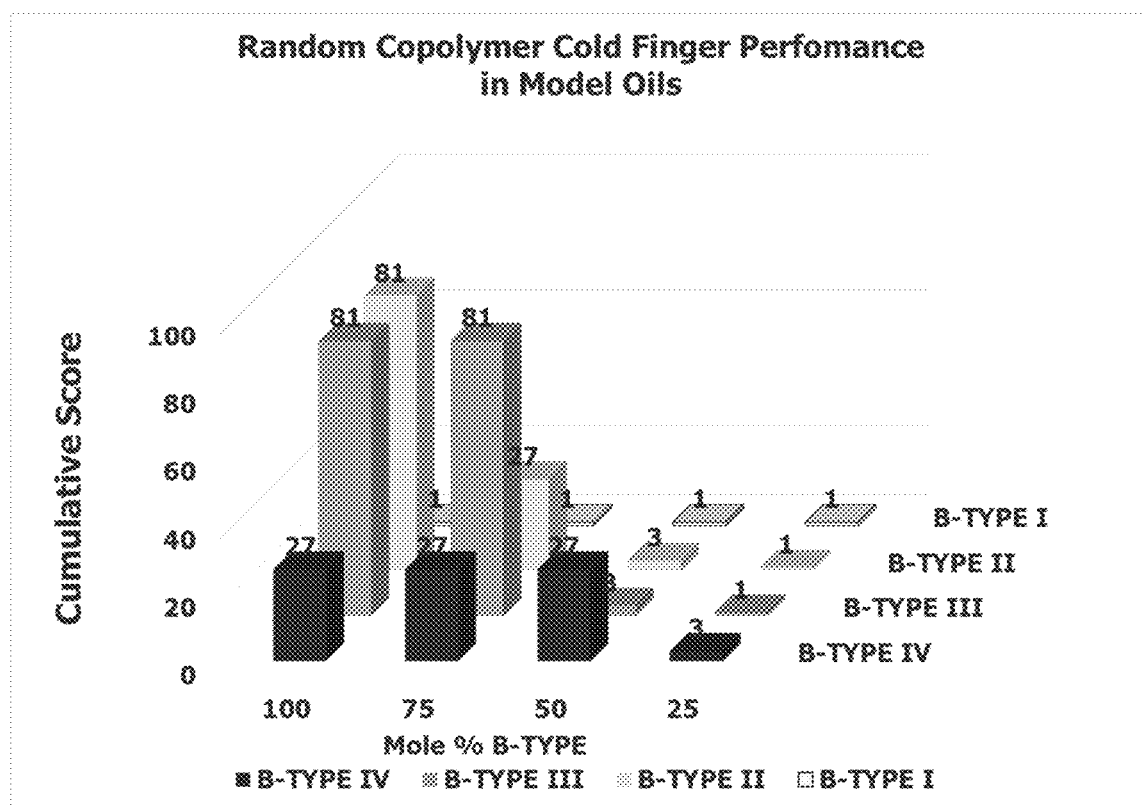
FIG. 4 is a graph showing the cumulative scoring results of Cold Finger testing for the random copolymer samples of Examples 1-16.
Figure 5:
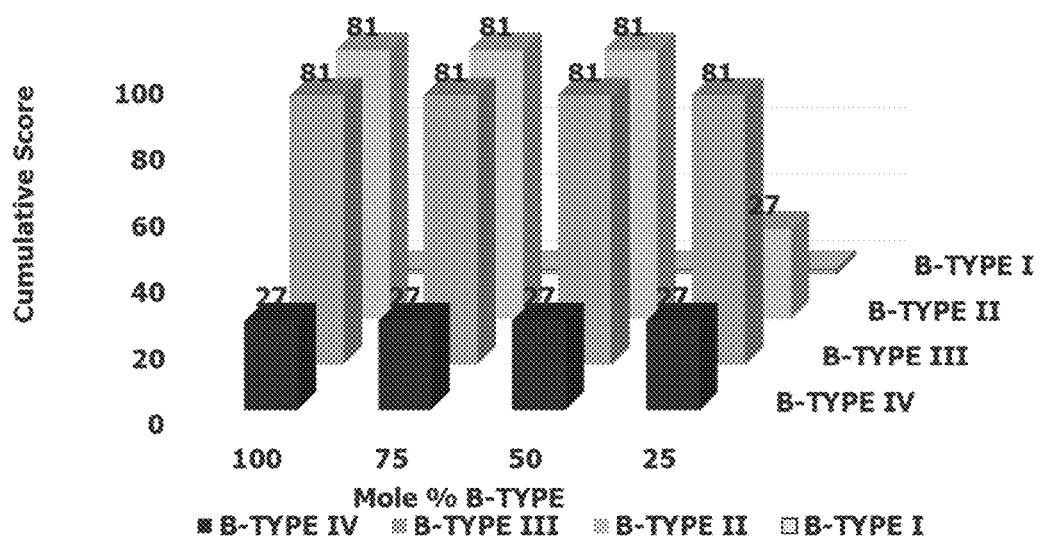
FIG. 5 is a graph showing the cumulative scoring results of Cold Finger testing for the block copolymer samples of Examples 17-25.

The underlying Cold Finger performance trends for the samples of Examples 1-25 copolymers are also shown graphically in FIGS. 3-5. As shown, the highest possible score was 81 followed by 27, 9, 3, and 1. For the random copolymers, the best performing additives were clustered in the region wherein they contain at least 75% Type B monomer (FIG. 4). For the block copolymers, there was a marked increase in performance for the entire range of polymers that contained 25% of the Type B monomer (FIG. 5). The same boost in performance was also observed for the block copolymers of 50% Type II and 50% Type III B monomers (FIG. 5).

No-flow point and time-to-gel testing was also performed for several of the samples using a 15% non-volatile residue ("NVR") percentage. The results are set forth below in Table 9.

TABLE 9

No-Flow Point and Time-To-Gel of 15% NVR Formulations

| Example | B-TYPE | POLYMER-TYPE | % B-TYPE | No-Flow Point$_{OSC}$ (°C.) | Time-to-Gel @ −20° C. | Time-to-Gel @ −30° C. |
|---|---|---|---|---|---|---|
| 2 | TYPE II | random | 100% | −14 | n.r. | n.r. |
| 3 | TYPE III | random | 100% | −2 | n.r. | n.r. |
| 4 | TYPE IV | random | 100% | 0 | n.r. | n.r. |
| 6 | TYPE II | random | 75% | −33 | 12272 | 285 |
| 7 | TYPE III | random | 75% | −20 | n.r. | n.r. |
| 8 | TYPE IV | random | 75% | −35 | 13000 | 0 |
| 10 | TYPE II | random | 50% | −38 | >4 hrs | 0 |
| 11 | TYPE III | random | 50% | −38 | >4 hrs | >4 hrs |
| 12 | TYPE IV | random | 50% | −38 | >4 hrs | >4 hrs |
| 17 | TYPE II | block | 75% | −26 | 7328 | 0 |
| 18 | TYPE III | block | 75% | −11 | n.r. | n.r. |
| 19 | TYPE IV | block | 75% | −38 | >4 hrs | 0 |
| 20 | TYPE II | block | 50% | −38 | >4 hrs | >4 hrs |
| 21 | TYPE III | block | 50% | −33 | >4 hrs | >4 hrs |
| 22 | TYPE IV | block | 50% | −38 | >4 hrs | >4 hrs |
| 23 | TYPE II | block | 25% | −38 | >4 hrs | >4 hrs |
| 24 | TYPE III | block | 25% | −38 | >4 hrs | >4 hrs |
| 25 | TYPE IV | block | 25% | −38 | >4 hrs | >4 hrs |

Two random copolymers (50% B-TYPE II and B-TYPE III) had no-flow point values of −38° C. and also passed the 4 hour time-to-gel evaluation at −20° C. and −30° C. Further, six out of the nine block copolymers were unexpectedly observed to have no-flow point values of −38° C. and also passed the 4 hour time-to-gel evaluation at −20° C. and −30° C.

The cloud point and pour point testing was also performed for Samples 17-19. In the analysis, the blank sample oil exhibited an average cloud point of 30.8° C. and an average pour point of 30° C. The results are set forth below in Table 10.

TABLE 10

Cloud Point and Pour Point

| Example | Dose (PPM) | B-TYPE | P-TYPE | % B-TYPE | CP (° C.) | PP (° C.) | ΔCP (° C.) | ΔPP (° C.) |
|---|---|---|---|---|---|---|---|---|
| 17 | 2000 | TYPE II | blocky | 75% | 28.0 | −39 | 2.8 | 69 |
| 17 | 1000 | TYPE II | blocky | 75% | 28.4 | −6 | 2.4 | 36 |
| 17 | 500 | TYPE II | blocky | 75% | 29.0 | 3 | 1.9 | 27 |
| 17 | 250 | TYPE II | blocky | 75% | 29.3 | 21 | 1.5 | 9 |
| 18 | 2000 | TYPE III | blocky | 75% | 28.3 | −24 | 2.5 | 54 |
| 18 | 1000 | TYPE III | blocky | 75% | 28.6 | −3 | 2.3 | 33 |
| 18 | 500 | TYPE III | blocky | 75% | 29.0 | 6 | 1.8 | 24 |
| 18 | 250 | TYPE III | blocky | 75% | 29.3 | 18 | 1.5 | 12 |
| 19 | 2000 | TYPE IV | blocky | 75% | 26.3 | 6 | 4.5 | 24 |
| 19 | 1000 | TYPE IV | blocky | 75% | 27.1 | 6 | 3.7 | 24 |
| 19 | 500 | TYPE IV | blocky | 75% | 27.9 | 15 | 2.9 | 15 |
| 19 | 250 | TYPE IV | blocky | 75% | 28.4 | 21 | 2.4 | 9 |

Each sample demonstrated a reduction in the cloud point and pour point. In particular, Examples 17 and 18 at a 2000 ppm dose exhibited a pour point of −39° C. and −24° C., respectively.

Example 26

Figure 6A:
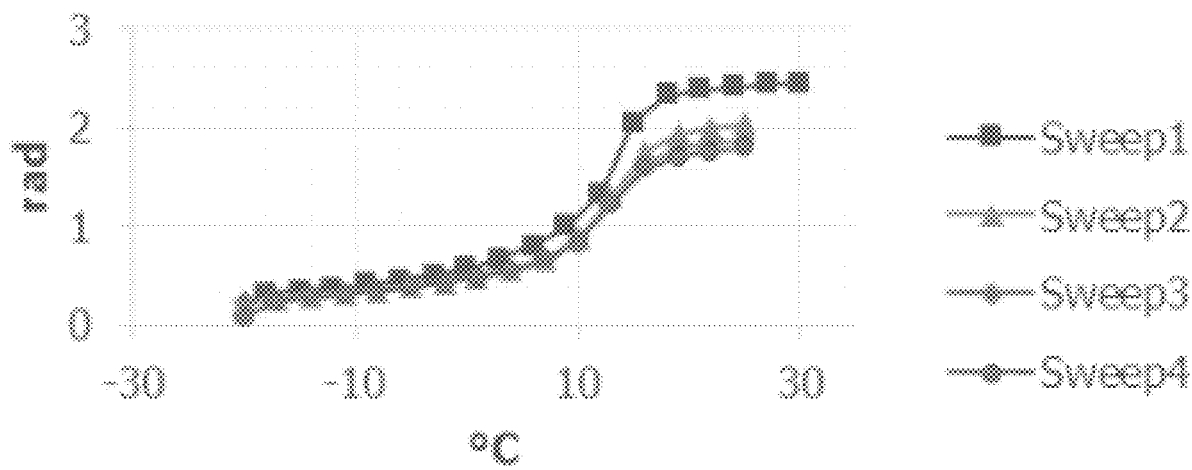
FIGS. 6A-6L are graphs of the oscillatory temperature sweeps of Examples 26 and 27.
Figure 6B:
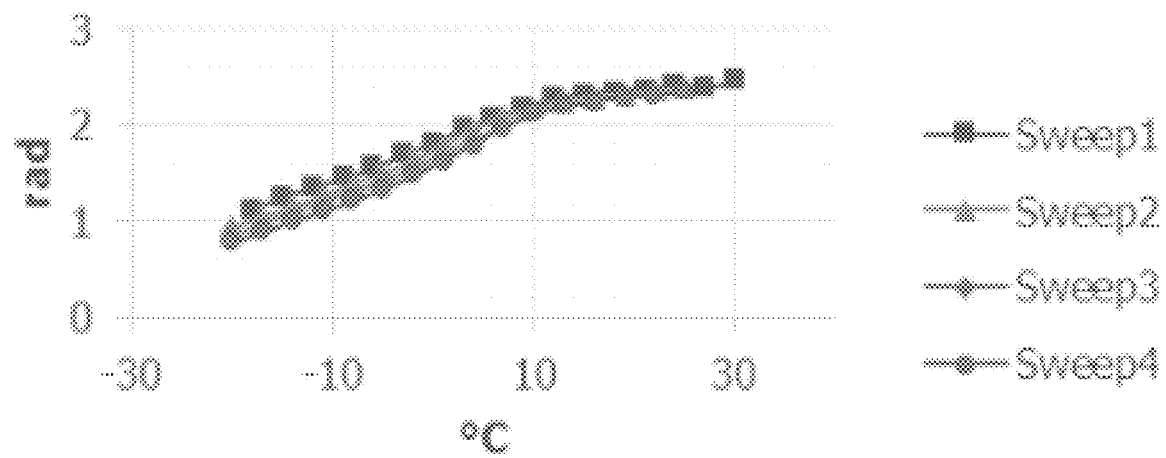
Figure 6C:
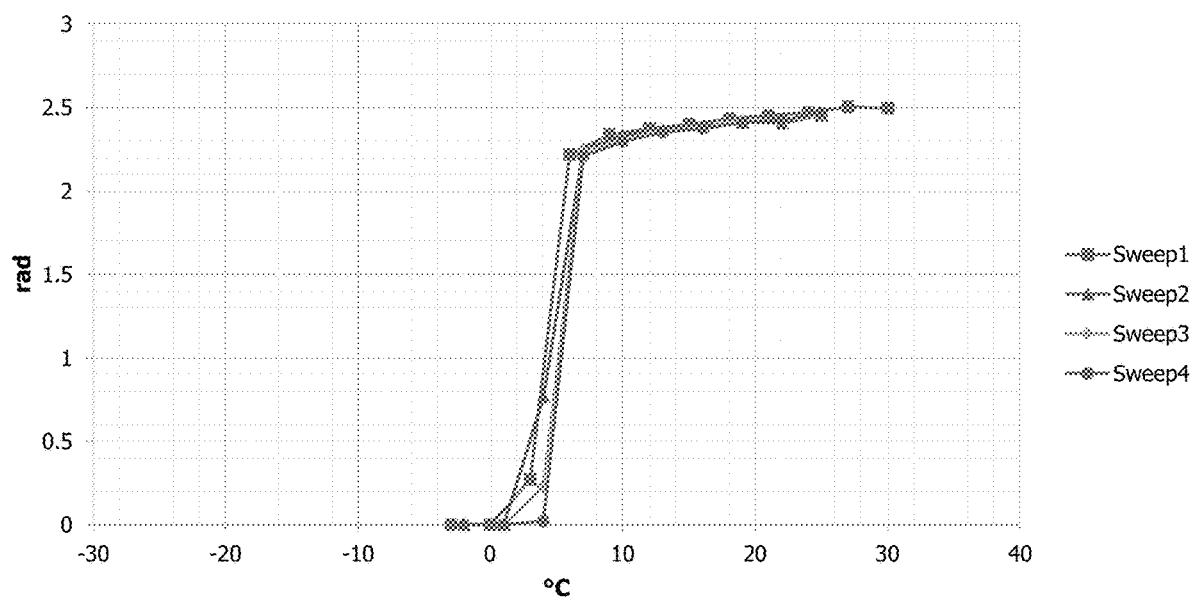
Figures 6D, 6E:
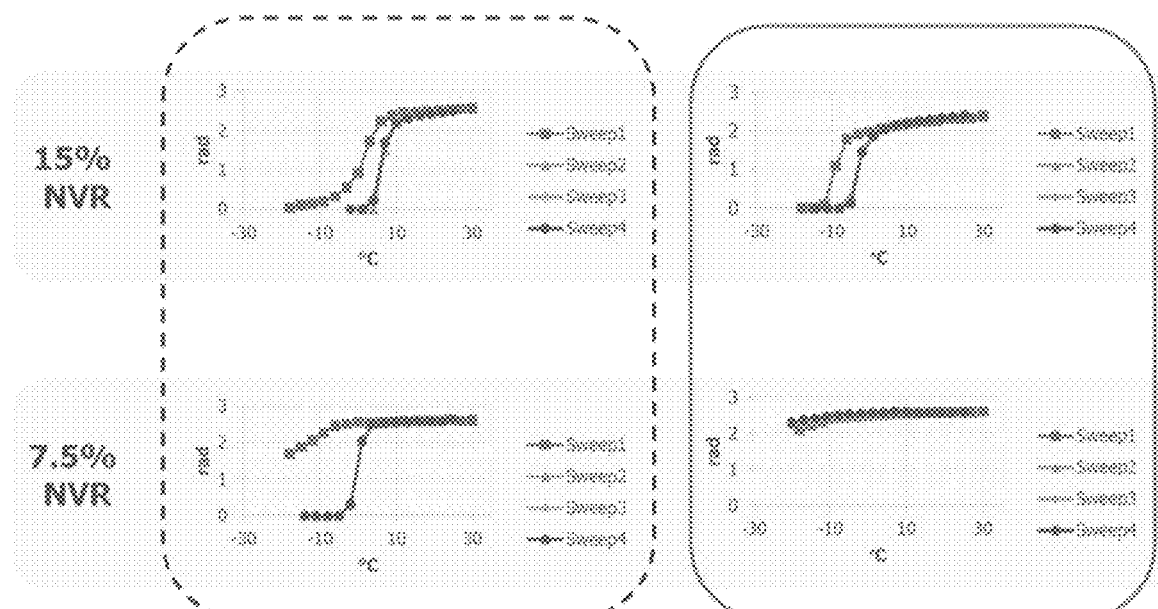
Figures 6F, 6G:
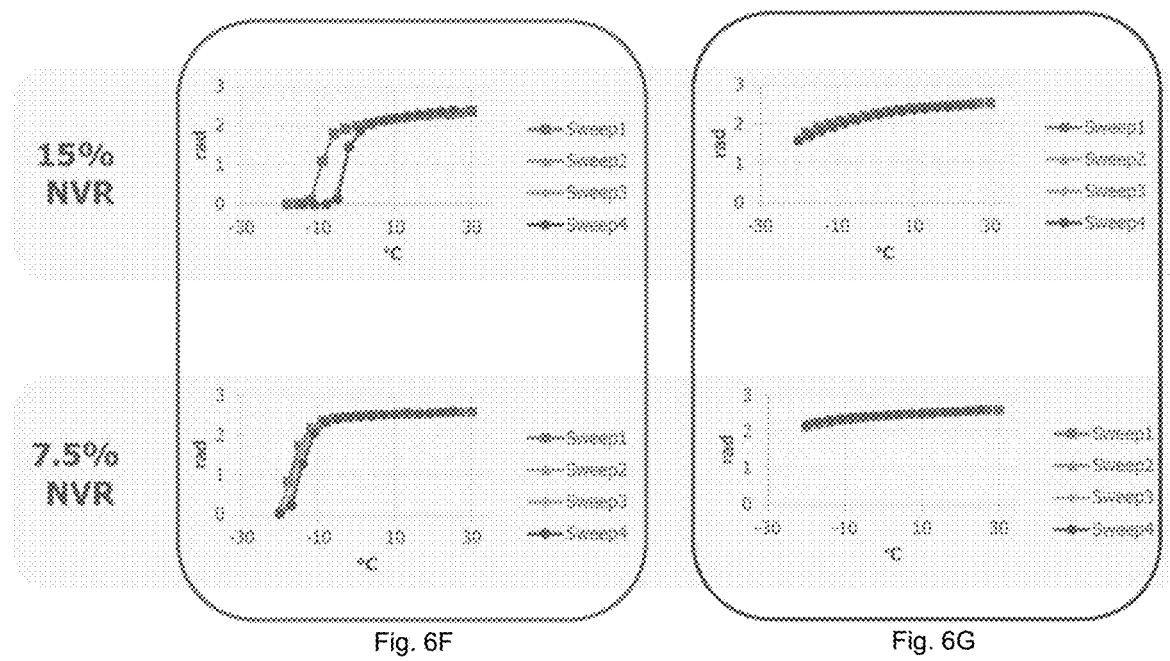
Figure 6H:
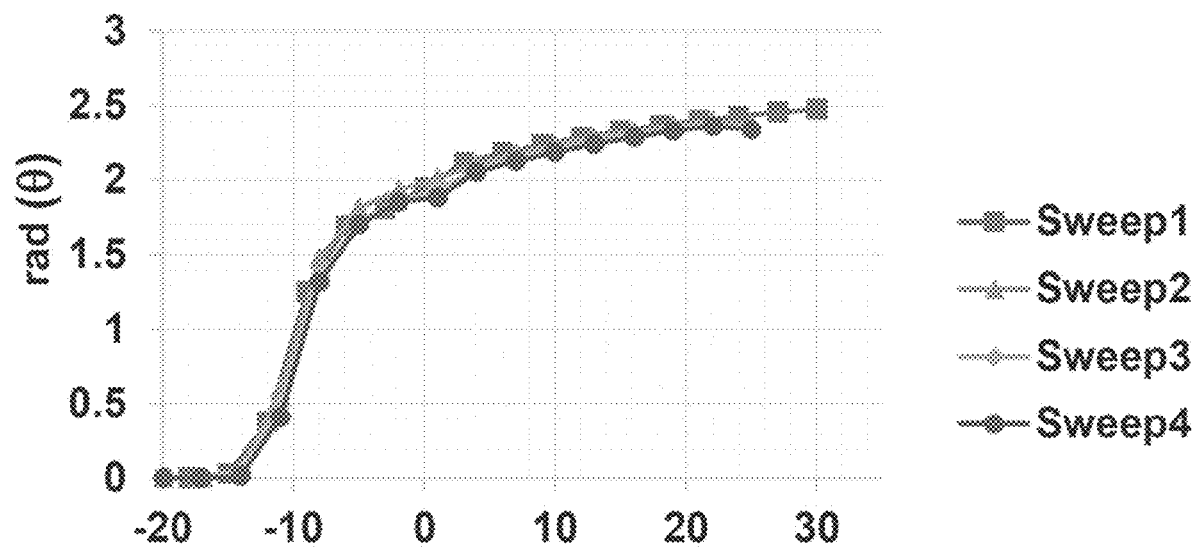
Figure 6I:
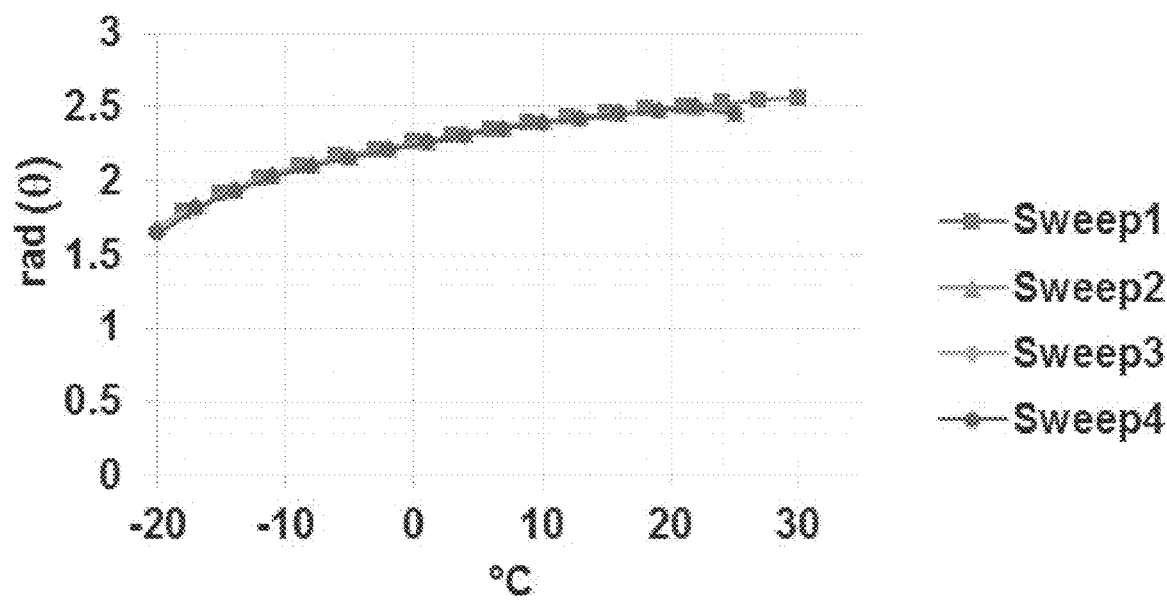
Figure 6J:
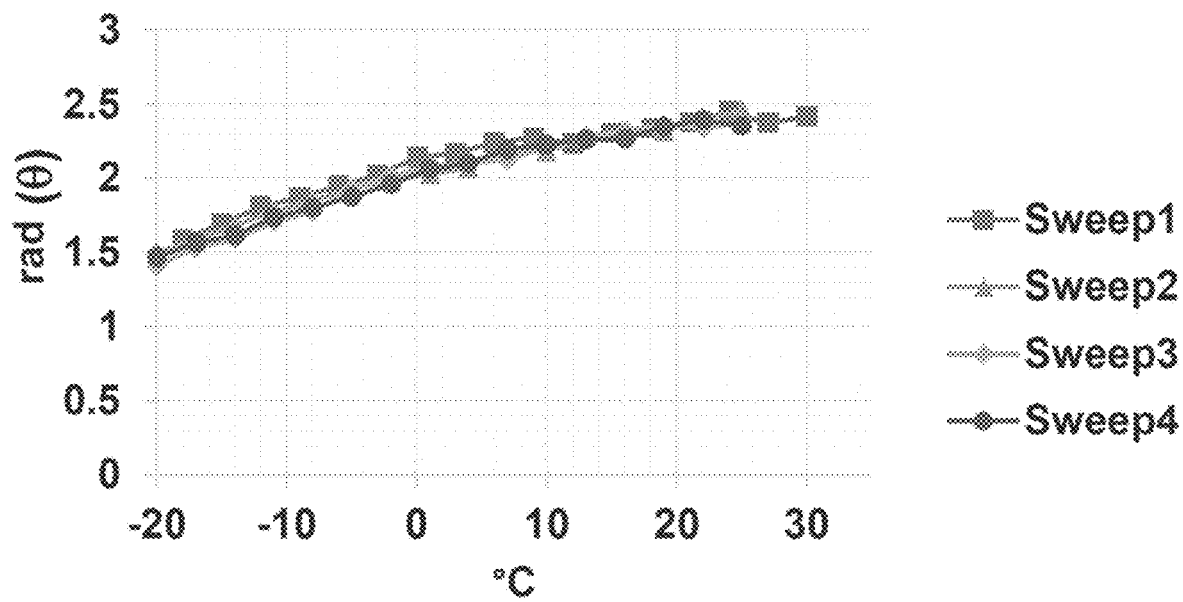
Figure 6K:
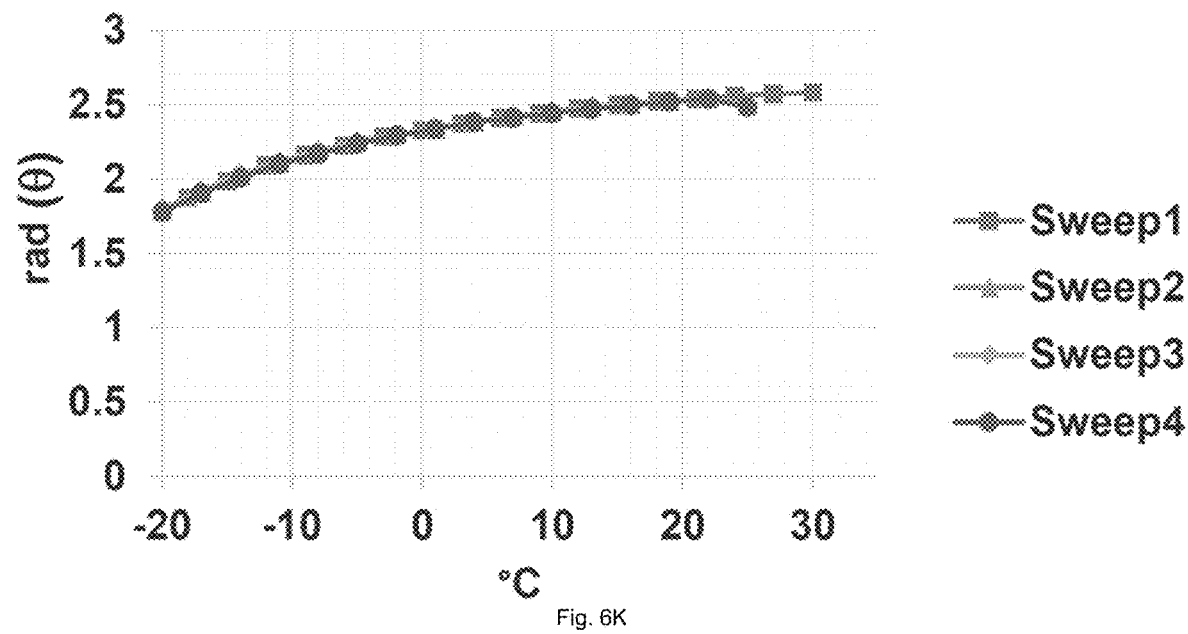
Figure 6L:
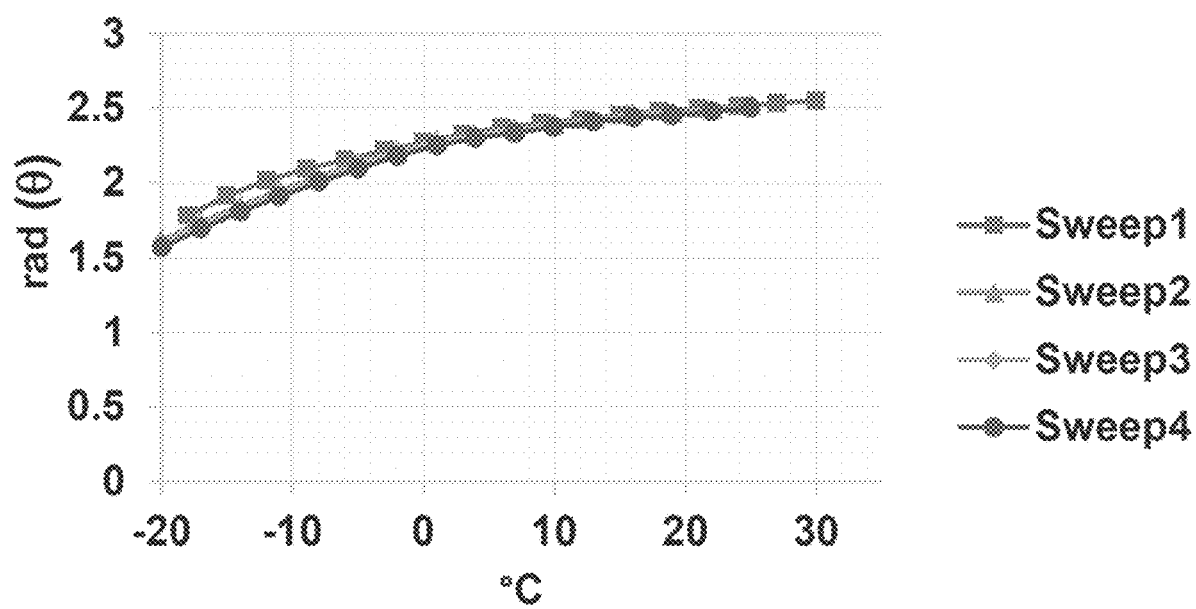

Oscillatory temperature sweeps were conducted with alkylphenol copolymers according to the present invention as well as other conventional alkylphenol polymers to assess their thermal stability upon undergoing several temperature cycles. In particular, FIGS. 6A and 6B illustrate oscillatory temperature sweeps of two alkylphenol copolymers at 15% NVR according to the present invention. The alkylphenol copolymer of FIG. 6A was formed from a combined mole ratio of 75:25 of the Type IV LCAP monomer to the Type A monomer (Example 19) and the alkylphenol copolymer of FIG. 6B was formed from a combined mole ratio of 25:75 of the Type IV LCAP monomer to the Type A monomer (Example 25). FIG. 6C illustrates oscillatory temperature sweeps of a conventional alkylphenol copolymer at 15% NVR. FIGS. 6D-6G illustrate oscillatory temperature sweeps of three other alkylphenol copolymers according to the present invention (FIGS. 6E-6G) and a conventional alkylphenol homopolymer (FIG. 6D) at 7.5% and 15% NVR. The alkylphenol polymer of FIG. 6D was a homopolymer of the Type II LCAP monomer (Example 2). The alkylphenol copolymers of FIGS. 6E-6G had the following combined mole ratio of the Type II LCAP monomer to the Type A monomer: 50:50 (FIG. 6E; Example 20), 75:25 (FIG. 6F; Example 17), and 25:75 (FIG. 6G; Example 23). As indicated by the data, the alkylphenol copolymers of the present invention exhibit an improved thermal cycling profile.

Example 27

Samples 17-25 were also diluted with a hydrocarbon solvent (A150 fluid) to form a composition containing about 15 wt. % of the respective random or block copolymer, and then dosed at a concentration of 1,000 ppm into Oil Fluid 6 as listed in Table 2. The Cold Finger paraffin inhibition was tested as set forth herein. In an effort to normalize the performance, a scoring system was also employed wherein any one additive is assigned three (3) points for reducing the wax deposit by at least 40% otherwise the additive is assigned one (1) point for failing to meet the 40% wax reduction metric. The results are set forth below in Table 11.

TABLE 11

Cold Finger - O6 Fluid

| Example | B-TYPE | % B-TYPE | POLYMER-TYPE | % reduction | Dose ppm | Score |
|---|---|---|---|---|---|---|
| 17 | TYPE II | 75% | block | 94 | 1000 | 3 |
| 18 | TYPE III | 75% | block | 94 | 1000 | 3 |
| 19 | TYPE IV | 75% | block | 57 | 1000 | 3 |
| 20 | TYPE II | 50% | block | 86 | 1000 | 3 |
| 21 | TYPE III | 50% | block | 92 | 1000 | 3 |
| 22 | TYPE IV | 50% | block | 53 | 1000 | 3 |
| 23 | TYPE II | 25% | block | 70 | 1000 | 3 |
| 24 | TYPE III | 25% | block | 66 | 1000 | 3 |
| 25 | TYPE IV | 25% | block | 72 | 1000 | 3 |

Oscillatory temperature sweeps were also conducted to assess their thermal stability upon undergoing several temperature cycles. In particular, FIGS. 6H-6L illustrate oscillatory temperature sweeps of Samples 18, 21, 25, 24, and 23, respectively. As indicated by the data, the alkylphenol copolymers of the present invention exhibit an improved thermal cycling profile.

Example 28

Samples 17, 20, and 23 were also diluted with a hydrocarbon solvent (A150 fluid) to form a composition containing about 15 wt. % of the respective random or block copolymer, and then dosed at a concentration ranging from 250 ppm to 2,000 ppm into Oil Fluid 7 as listed in Table 2. The Cold Finger paraffin inhibition was tested as set forth herein. In an effort to normalize the performance, a scoring system was also employed wherein any one additive is assigned three (3) points for reducing the wax deposit by at least 40% otherwise the additive is assigned one (1) point for failing to meet the 40% wax reduction metric. The results are set forth below in Table 12.

TABLE 12

Cold Finger - O7 Fluid

| Example | B-TYPE | % B-TYPE | POLYMER-TYPE | % reduction | Dose ppm | Score |
|---|---|---|---|---|---|---|
| 20 | TYPE-II | 75% | block | 41 | 250 | 3 |
| 20 | TYPE-II | 75% | block | 72 | 500 | 3 |
| 20 | TYPE-II | 75% | block | 73 | 1000 | 3 |
| 20 | TYPE-II | 75% | block | 70 | 2000 | 3 |
| 17 | TYPE-II | 50% | block | 77 | 250 | 3 |
| 17 | TYPE-II | 50% | block | 69 | 500 | 3 |
| 17 | TYPE-II | 50% | block | 73 | 1000 | 3 |
| 17 | TYPE-II | 50% | block | 66 | 2000 | 3 |
| 23 | TYPE-II | 25% | block | 30 | 250 | 1 |
| 23 | TYPE-II | 25% | block | 23 | 500 | 1 |
| 23 | TYPE-II | 25% | block | 69 | 1000 | 3 |
| 23 | TYPE-II | 25% | block | 70 | 2000 | 3 |

Prophetic Example 1

A block copolymer may be formed as described in Example 17, except that $C_9$ alkyl phenol can be used instead of Type II LCAP.

Prophetic Example 2

A block copolymer may be formed as described in Example 17, except that $C_4$ alkyl phenol can be used instead of Type II LCAP.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An alkylphenol copolymer comprising at least two different alkylphenol monomers, wherein the alkylphenol copolymer exhibits the following:
   an oscillation displacement Θ of greater than 0 at a temperature of −5° C. in a first oscillation temperature sweep, and
   an oscillation displacement Θ in a second oscillation temperature sweep within 25% of the oscillation displacement Θ in the first oscillation temperature sweep at a temperature of −5° C.,
   wherein the first oscillation temperature sweep starts at 30° C. and ends at either −20° C. or an oscillation displacement Θ of 0 and is conducted with a stress of 0.4 Pa at an angular frequency of 0.25 rad/s and each subsequent oscillation temperature sweep starts at 25° C. and ends at either −20° C. or an oscillation displacement Θ of 0 and is conducted with a stress of 0.4 Pa at an angular frequency of 0.25 rad/s,
   wherein at least one of the at least two different alkylphenol monomers as the following repeating unit (B):

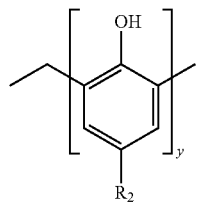

(B)

wherein,
   y is an integer from 1 to 200; and
   $R_2$ includes a straight or branched $C_{22}$-$C_{40}$ alkyl.

2. The alkylphenol copolymer of claim 1, wherein the oscillation displacement Θ in the second oscillation temperature sweep is within 20% of the oscillation displacement Θ in the first oscillation temperature sweep.

3. The alkylphenol copolymer of claim 1, wherein the oscillation displacement Θ in the second oscillation temperature sweep is within 5% of the oscillation displacement Θ in the first oscillation temperature sweep.

4. The alkylphenol copolymer of claim 1, wherein the oscillation displacement Θ in a third oscillation temperature sweep is within 25% of the oscillation displacement Θ in the first oscillation temperature sweep at a temperature of −5° C.

5. The alkylphenol copolymer of claim 1, wherein the oscillation displacement Θ in a fourth oscillation temperature sweep is within 25% of the oscillation displacement Θ in the first oscillation temperature sweep at a temperature of −5° C.

6. The alkylphenol copolymer of claim 1, wherein the oscillation displacement Θ in the second oscillation temperature sweep is within 25% of the oscillation displacement Θ in the first oscillation temperature sweep at a temperature of −10° C.

7. The alkylphenol copolymer of claim 1, wherein the oscillation displacement Θ in the first oscillation temperature sweep is greater than 0 at a temperature of −20° C.

8. The alkylphenol copolymer of claim 1, wherein the oscillation displacement Θ in the first oscillation temperature sweep is greater than 0 at a temperature of −40° C.

9. The alkylphenol copolymer of claim 1, wherein the other of the at least two different alkylphenol monomers of the alkylphenol copolymer comprises the following repeating unit (A):

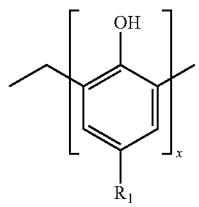

(A)

wherein,
   x is an integer from 1 to 200; and
   $R_1$ includes a straight or branched $C_1$-$C_{40}$ alkyl.

10. The alkylphenol copolymer of claim 1, wherein the other of the at least two different alkylphenol monomers of the alkylphenol copolymer comprises the following repeating unit (A):

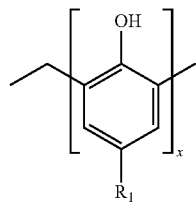

wherein,
x is an integer from 1 to 200; and
$R_1$ includes a straight or branched $C_1$-$C_{15}$ alkyl.

11. The alkylphenol copolymer of claim 1, wherein the oscillation displacement Θ in the second oscillation temperature sweep is within 10% of the oscillation displacement Θ in the first oscillation temperature sweep.

12. The alkylphenol copolymer of claim 1, wherein the oscillation displacement Θ in the second oscillation temperature sweep is within 25% of the oscillation displacement Θ in the first oscillation temperature sweep at a temperature of −15° C.

13. The alkylphenol copolymer of claim 1, wherein the oscillation displacement Θ in a third oscillation temperature sweep is within 25% of the oscillation displacement Θ in the first oscillation temperature sweep at a temperature of −10° C. and wherein the oscillation displacement Θ in a fourth oscillation temperature sweep is within 25% of the oscillation displacement Θ in the first oscillation temperature sweep at a temperature of −10° C.

14. The alkylphenol copolymer of claim 1, wherein the alkylphenol copolymer is a block copolymer.

15. The alkylphenol copolymer of claim 1, wherein the alkylphenol copolymer exhibits an asphaltene dispersancy parameter of about 500 or less as determined at a non-volatile residue percentage of 15% and/or wherein the alkylphenol copolymer exhibits a percent asphaltene dispersancy of about 80% or more as determined at a non-volatile residue percentage of 15%.

16. The alkylphenol copolymer of claim 1, wherein the alkylphenol copolymer exhibits a Cold Finger paraffinic wax inhibition of about 60% or more.

17. The alkylphenol copolymer of claim 1, wherein the oscillation temperature sweeps are conducted in a composition consisting essentially of the alkylphenol copolymer and a hydrocarbon solvent at a non-volatile residue concentration of 15%.

\* \* \* \* \*